US006946579B2

(12) United States Patent
Godfrey et al.

(10) Patent No.: US 6,946,579 B2
(45) Date of Patent: Sep. 20, 2005

(54) ARYLPIPERAZINES HAVING ACTIVITY AT THE SEROTONIN $1_A$ RECEPTOR

(75) Inventors: Alexander Glenn Godfrey, Greenwood, IN (US); Daniel Timothy Kohlman, Indianapolis, IN (US); John Cunningham O'Toole, Indianapolis, IN (US); Yao-Chang Xu, Fishers, IN (US); Tony Yantao Zhang, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 10/613,798

(22) Filed: Jul. 2, 2003

(65) Prior Publication Data

US 2004/0049083 A1 Mar. 11, 2004

Related U.S. Application Data

(62) Division of application No. 10/022,045, filed on Dec. 18, 2001, now Pat. No. 6,645,967, which is a division of application No. 09/753,645, filed on Jan. 3, 2001, now Pat. No. 6,358,958, which is a division of application No. 09/208,553, filed on Dec. 9, 1998, now Pat. No. 6,239,135.
(60) Provisional application No. 60/089,589, filed on Jun. 17, 1998, provisional application No. 60/069,791, filed on Dec. 16, 1997, and provisional application No. 60/069,722, filed on Dec. 16, 1997.

(51) Int. Cl.$^7$ ............................................. C07C 49/312
(52) U.S. Cl. ........................ 568/377; 568/312; 568/313; 568/320; 568/349; 568/376
(58) Field of Search ............................... 568/312, 313, 568/320, 349, 376, 377

(56) References Cited

U.S. PATENT DOCUMENTS

| | | | |
|---|---|---|---|
| 4,536,516 A | 8/1985 | Harper et al. ................ | 514/514 |
| 4,988,814 A | 1/1991 | Abou-Gharbia et al. .... | 544/295 |
| 5,292,732 A | * 3/1994 | Rover ......................... | 514/249 |
| 5,340,812 A | 8/1994 | Cliffe ......................... | 514/255 |
| 5,346,896 A | 9/1994 | Ward et al. .................. | 514/252 |
| 5,541,326 A | 7/1996 | Cliffe ......................... | 544/392 |
| 5,614,523 A | 3/1997 | Audia et al. ................. | 514/252 |
| 5,693,642 A | 12/1997 | Cliffe et al. ................. | 514/252 |

FOREIGN PATENT DOCUMENTS

| | | |
|---|---|---|
| BE | 637389 | 3/1964 |
| CN | 1076446 A | 9/1993 |
| EP | 0512755 | 11/1992 |
| EP | 0521368 | 1/1993 |
| EP | 0661266 A1 | 7/1995 |
| GB | 2248499 A | 4/1992 |
| GB | 2303303 A | 2/1997 |
| WO | WO 92/06082 A | 4/1992 |
| WO | WO 92/06082 | 4/1992 |
| WO | WO 94/21610 | 9/1994 |

OTHER PUBLICATIONS

Paquette, L. A. et al., "Intramolecular Nucleophillic Addition to Unsaturated Carbon. Dependence of Cyclization Efficiency on the Method of Carbon–Carbon Bond Cleavage Utilized To Generate the Reactive Species", J. Org. Chem. 1989, 54, pp. 5044–5053.*
ID Patent Fast Alert, Jul. 1997, citing GB 2303303A.
Morren, H. et al., Industrie Chimique Belge, 28(2), 123 (1963).
Rasmussen, K. and V. Rocco, Annual Reports Med. Chem., 30(1), 1 (1995).
E. Diez–Barra et al., Tetrahedron, 53(33), 11437–11448 (1997).
E. C. Dodds et al., Proceedings of the Royal Society of London, Series B; Biological Sciences, 127, 140–167 (1939).
T. Kawabata et al., Journal of the American Chemical Society, 113(25), 9694–9696 (1991).
Chemical Abstracts, 115(26), Dec. 30 1991, Abstract No. 280741k.
Heme, Hans–George, Justus Liebigs Annalen Der Chemie, 735, 56–64 (1970).
Saxena, Pramod R. Pharmac. Ther., 66, 339–368 (1995).
Robichaud et al., Annual Reports in Medicinal Chemistry, 11–20 (2000).

* cited by examiner

Primary Examiner—Dwayne Jones
(74) Attorney, Agent, or Firm—Knobbe Martens Olson & Bear LLP

(57) ABSTRACT

A series of aryl piperazine compounds are effective pharmaceuticals for the treatment of conditions related to or affected by the serotonin $1_A$ receptor; the compounds are particularly effective antagonists at that receptor, and are particularly useful for alleviating the symptoms of nicotine and tobacco withdrawal.

5 Claims, No Drawings

ARYLPIPERAZINES HAVING ACTIVITY AT THE SEROTONIN $1_A$ RECEPTOR

CROSS REFERENCE

This application is a division of application Ser. No. 10/022,045, filed Dec. 18, 2001, now U.S. Pat. No. 6,645,967 which is a division of application Ser. No. 09/753,645, filed Jan. 3, 2001, now U.S. Pat. No. 6,358,958, which is a division of Ser. No. 09/208,553 filed Dec. 9, 1998, now U.S. Pat. No. 6,239,135, which claims the benefit of U.S. Provisional Application Nos. 60/069,722 filed Dec. 16, 1997, 60/069,791 filed Dec. 16, 1997 and 60/089,589 filed Jun. 17, 1998.

FIELD OF THE INVENTION

The present invention belongs to the fields of pharmacology and medicinal chemistry, and provides new pharmaceuticals which are useful for the treatment of diseases which are caused or affected by disorders of the serotonin-affected neurological systems, particularly those relating to the $1_A$ receptor.

BACKGROUND OF THE INVENTION

Pharmaceutical researchers have discovered in recent years that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generations of serotonin-affecting drugs tended to have a variety of different physiological functions, considered from both the mechanistic and therapeutic points of view. More recently, it has become possible to study the function of drugs at individual receptors in vitro or ex vivo, and it has also been realized that therapeutic agents with a single mechanism of action are often advantageous to the patient. Accordingly, the objective of research now is to discover not only agents which affect only functions of serotonin, but agents which affect only a single function of serotonin, at a single identifiable receptor.

The present invention provides compounds which have highly selective activity as antagonists of the serotonin $1_A$ receptor.

SUMMARY OF THE INVENTION

The present invention provides a series of new aryl piperazine compounds, methods of using them for pharmaceutical purposes, and pharmaceutical compositions whereby the compounds may be conveniently administered.

The invention also provides methods of antagonizing, the 5HT-$1_A$ receptor, and therapeutic methods which are related to their effect on the 5HT-$1_A$ receptor. Such methods of treatment include, particularly, methods of alleviating the symptoms caused by withdrawal or partial withdrawal from the use of tobacco or of nicotine, comprising the administration to a patient in need of such treatment of a compound of Formula I

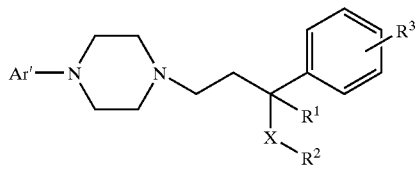

wherein
Ar' is a mono- or bi-cyclic aryl or heteroaryl radical substituted with one to three substituents selected from the group consisting of hydrogen, $(C_1-C_6)$alkyl, $(C_1-C_6)$alkoxy, $(C_1-C_6)$alkylthio, $(C_2-C_6)$alkenyl, $(C_2-C_6)$alkynyl, $(C_1-C_6)$ alkylhalo, $(C_3-C_8)$cycloalkyl, $(C_3-C_8)$cycloalkenyl or halo;

$R^1$ is hydrogen, $(C_1-C_6)$alkyl, $(C_1-C_6)$alkoxy, $(C_1-C_6)$alkylthio;

$R^2$ is phenyl, naphthyl or $(C_3-C_{12})$cycloalkyl substituted with one or two substituents selected from the group consisting of hydrogen, $(C_1-C_6)$alkyl, $(C_1-C_6)$alkoxy, $(C_1-C_6)$ alkylthio, $(C_2-C_6)$alkenyl, $(C_2-C_6)$alkynyl, $(C_1-C_6)$ alkylhalo, $(C_3-C_8)$cycloalkyl, $(C_3-C_8)$cycloalkenyl or halo;

$R^3$ is selected from the group consisting of hydrogen, $(C_1-C_6)$alkyl, $(C_1-C_6)$alkoxy, $(C_1-C_6)$alkylthio, $(C_2-C_6)$ alkenyl, $(C_2-C_6)$alkynyl, $(C_1-C_6)$alkylhalo, $(C_3-C_8)$ cycloalkyl, $(C_3-C_8)$cycloalkenyl or halo;

X is —C(=O)—, —CHOH— or —CH$_2$—;

or a pharmaceutically acceptable salt, racemate, optical isomer or solvate thereof.

Further, such therapeutic methods include methods of treatment of anxiety, depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine.

A further treatment method provided by the present invention is a method for potentiating the action of a serotonin reuptake inhibitor, comprising administering to a patient an effective amount of a compound of Formula I in combination with the serotonin reuptake inhibitor.

More specifically, the present invention provides compounds of formula Ia;

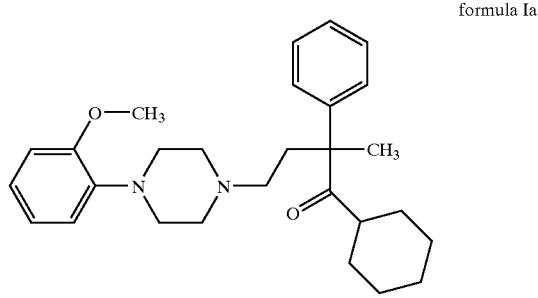

formula Ia or the pharmaceutically acceptable salts thereof.

The compounds of formula Ia are enclosed within the scope of the compounds of Formula I and are therefore useful for the methods described herein for Formula I. For example, the present invention provides methods of antagonizing, the 5HT-$1_A$ receptor, and therapeutic methods which are related to their effect on the 5HT-$1_A$ receptor. Such methods of treatment include, particularly, methods of alleviating the symptoms caused by withdrawal or partial withdrawal from the use of tobacco or of nicotine, comprising the administration to a patient in need of such treatment, an effective amount of a compound of formula Ia. Further, such therapeutic methods include methods of treatment of anxiety, depression, hypertension, cognitive disorders, psychosis, sleep disorders, gastric motility disorders, sexual dysfunction, brain trauma, memory loss, eating disorders and obesity, substance abuse, obsessive-compulsive disease, panic disorder and migraine.

In addition, the present invention provides a method for potentiating the action of a serotonin reuptake inhibitor, comprising administering to a patient an effective amount of a compound of formula Ia in combination with the serotonin reuptake inhibitor.

The invention further provides a method of assisting a patient in ceasing or reducing their use of tobacco or nicotine comprising administering to a patient an effective amount of a compound of the Formula I or formula Ia.

This invention also encompasses novel processes for the synthesis of the compounds of formula I and formula Ia, the synthesis of novel intermediates thereof, and further encompasses novel intermediates per se.

DESCRIPTION OF PREFERRED EMBODIMENTS

In the present document, all descriptions of concentrations, amounts, ratios and the like will be expressed in weight units unless otherwise stated. All temperatures are in degrees Celsius.

The Compounds

It is believed that the general description of the compounds above is sufficient to explain their nature to the skilled reader; attention to the Examples which follow is also encouraged. Some additional description will be provided to assure that no misunderstanding occurs.

In the general description, the general chemical terms are all used in their normal and customary meanings. For example, the small alkyl and alkoxy groups, such as $(C_1-C_6)$ alkyl and $(C_1-C_6)$alkoxy groups include, depending on the size of the groups, methyl, ethyl, propyl, isopropyl, n-butyl, s-butyl, pentyl, 3-methylbutyl, hexyl, and branched hexyl groups, and the corresponding alkoxy groups, as may be allowed by the individually named groups. Where a number of possible substituent groups are permitted on a group, such as the one to three alkyl, alkoxy or halo groups permitted on an Ar group, it will be understood by the reader that only substitution which is electronically and sterically feasible is intended.

The term "alkenyl" as used herein represents an unsaturated branched or linear group having at least one double bond. Examples of such groups include radicals such as vinyl, allyl, 2-butenyl, 3-butenyl, 2-pentenyl, 3-pentenyl, 4-pentenyl, 2-hexenyl, 3-hexenyl, 4-hexenyl, 5-hexenyl as well as dienes and trienes of straight and branched chains.

The term "alkynyl" denotes such radicals as ethynyl, propynyl, butynyl, pentynyl, hexynyl as well as di- and tri-ynes.

The term "$(C_1-C_6)$alkylthio" defines a straight or branched alkyl chain having one to six carbon atoms attached to the remainder of the molecule by a sulfur atom. Typical $(C_1-C_6)$alkylthio groups include methylthio, ethylthio, propylthio, butylthio, pentylthio, hexylthio and the like.

The term "$(C_1-C_6)$alkylhalo" refers to alkyl substituents having one or more independently selected halo atoms attached at one or more available carbon atoms. These terms include chloromethyl, bromoethyl, trifluoroethyl, trifluoromethyl, 3-bromopropyl, 2-bromopropyl, 3-chlorobutyl, 2,3-dichlorobutyl, 3-chloro-2-bromo-butyl, trichloromethyl, dichloroethyl, 1,4-dichlorobutyl, 3-bromopentyl, 1,3-dichlorobutyl, 1,1-dichloropropyl, and the like. More preferred $(C_1-C_6)$alkylhalo groups are trichloromethyl, trichloroethyl, and trifluoromethyl. The most preferred $(C_1-C_6)$alkylhalo is trifluoromethyl.

The term "$(C_3-C_8)$cycloalkyl" includes groups such as cyclopropyl, cyclobutyl, cyclopentyl, cyclohexyl, cycloheptyl and cyclooctyl. The term "$(C_3-C_8)$cycloalkyl" includes $(C_3-C_6)$cycloalkyl.

The term "$(C_3-C_8)$cycloalkenyl" represents an olefinically unsaturated ring having 3 to 8 carbon atoms including groups such as cyclopropenyl, cyclobutenyl, cyclopentenyl, cyclohexenyl, cycloheptenyl, cyclooctenyl, and the like. The term "$(C_3-C_8)$cycloalkenyl" includes $(C_3-C_6)$cycloalkenyl.

The term "aryl" represents phenyl or naphthyl.

The term "bicyclic" represents either an unsaturated or saturated stable 7- to 12-membered bridged or fused bicyclic carbon ring. The bicyclic ring may be attached at any carbon atom which affords a stable structure. The term includes, but is not limited to, naphthyl, dicyclohexyl, dicyclohexenyl, and the like.

The term, "mono or bicyclic heteroaryl radical", refers to radicals derived from monocyclic or polycyclic, aromatic nuclei having 5 to 14 ring atoms and containing from 1 to 3 hetero atoms selected from the group consisting of nitrogen, oxygen or sulfur. Typical heterocyclic radicals are pyrrolyl, furanyl, thiophenyl, pyrazolyl, imidazolyl, indolizinyl, isoquinolyl, benzothienyl, isoindolizinyl, oxazolyl, indolyl, carbazolyl, norharmanyl, azaindolyl, dibenzofuranyl, thianaphthenyl, dibenzothiophenyl, indazolyl, imidazo(1.2-A)pyridinyl, anthranilyl, purinyl, pyridinyl, phenylpyridinyl, pyrimidinyl, pyrazinyl, quinolinyl.

The terms "halo" or "halide" are used in the above formula to refer to fluoro, chloro, bromo or iodo.

The term "aprotic solvent" refers to polar solvents of moderately high dielectric constant which do not contain an acidic hydrogen. Examples of common aprotic solvents are dimethylsulfoxide (DMSO), dimethylformamide, sulfolane, tetrahydrofuran, diethyl ether, methyl-t-butyl ether, or 1,2-dimethoxyethane.

The term "protic solvent" refers to a solvent containing hydrogen that is attached to oxygen, and hence is appreciably acidic. Common protic solvents include such solvents as water, methanol, ethanol, 2-propanol, and 1-butanol.

The term "inert atmosphere" refers to reaction conditions in which the mixture is covered with a layer of inert gas such as nitrogen or argon.

As used herein, the term "Me" refers to a —$CH_3$ group, the term "Et" refers to a —$CH_2CH_3$ group and the term "Pr" refers to a —$CH_2CH_2CH_3$ group.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. As used herein, the term "optical isomer" is equivalent to the term "enantiomer". The terms "racemate", "racemic mixture" or "racemic modification" refer to a mixture of equal parts of enantiomers. The term "chiral center" refers to a carbon atom to which four different groups are attached.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formulas I or Ia can be resolved by one of ordinary skill in the art using standard techniques well known in the art, such as those described by J. Jacques, et al., "Enantiomers, Racemates, and Resolutions", John Wiley and Sons, Inc., 1981. Examples of resolutions include recrystallization techniques or chiral chromatography.

The compounds of Formula I and formula Ia, as a class are highly active, important and particularly useful in the treatment methods of the present invention, but certain classes of the compounds are preferred. The following paragraphs describe such preferred classes. It will be understood that the preferred classes are applicable both to the treatment methods and to the new compounds of the present invention.

The reader will understand that the preferred classes of compounds may be combined to form additional, broader or narrower classes of preferred compounds.

a) Ar' is phenyl or pyridyl;
b) Ar' is naphthyl;
c) Ar' is pyrazinyl, pyrimidinyl, pyrrolyl, furyl, thienyl, indolyl, purinyl, imidazolyl, pyrazolyl, indolizinyl, benzofuranyl, isoquinolyl, quinolyl, benzothienyl or isoindolizinyl;
d) Ar' is optionally substituted with $(C_1-C_6)$alkyl, $(C_1-C_6)$alkoxy, halo, $(C_2-C_6)$alkenyl or $(C_2-C_6)$alkynyl;
e) Ar' is optionally substituted with $(C_1-C_4)$alkyl, $(C_1-C_4)$alkoxy or halo;
f) $R^1$ is hydrogen;
g) $R^1$ is $(C_1-C_6)$alkyl or $(C_1-C_6)$alkoxy;
h) $R^1$ is $(C_1-C_2)$alkyl or $(C_1-C_2)$alkoxy;
i) $R^2$ is phenyl;
j) $R^2$ is $(C_3-C_8)$cycloalkyl;
k) $R^2$ is $(C_3-C_6)$cycloalkyl;
l) $R^2$ is cyclohexyl;
m) $R^3$ is $(C_1-C_6)$alkyl, $(C_1-C_6)$alkoxy or halo;
n) $R^3$ is $(C_1-C_4)$alkyl, $(C_1-C_4)$alkoxy or halo;
o) X is —C=O;
p) X is —CHOH; and
q) X is —CH$_2$.
r) formula Ia
s) the enantiomer of formula Ia wherein the $[\alpha]^D_{20}$ in methanol is (+).

Since the compounds of this invention are basic in nature, they accordingly react with any of a number of inorganic and organic acids to form pharmaceutically acceptable acid addition salts. Included within the scope of the invention are the mono- and di-salts. Acids commonly employed to form such salts are inorganic acids such as hydrochloric acid, hydrobromic acid, hydroiodic acid, sulfuric acid, phosphoric acid, and the like, and organic acids, such as p-toluenesulfonic acid, methanesulfonic acid, oxalic acid, p-bromophenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are the monohydrochloride, dihydrochloride, monohydrobromide, dihydrobromide, Formula I/succinate (1:1), formula Ia/succinate(1:1), Formula I/succinate 2:1, formula Ia/succinate 2:1, phosphate, d-tartrate, l-tartrate or maleate. It is understood by one of ordinary skill that hydrates of the free base or of the pharmaceutically acceptable salts are included within the scope of the present invention.

Many of the compounds of Formula I, including formula Ia, are optical isomers. For example, the compounds have an asymmetric center (or chiral center) at the carbon atom to which $R^1$ and X are attached. However, when a compound of the present invention is named without an indication of asymmetric form, any and all of the possible asymmetric forms are intended. This invention is not limited to any particular isomer but includes all possible individual isomers and racemates.

The intermediates and final products may be isolated and purified by conventional techniques, such as, purification with chromatography using silica gel or recrystallization of crystalline isolates.

It will be readily appreciated by the skilled artisan that the starting materials which are not described are either commercially available or can be readily prepared by known techniques from commercially available starting materials. All other reactants used to prepare the compounds in the instant invention are commercially available.

The compounds of the invention are generally prepared according to the following schemes.

Scheme I

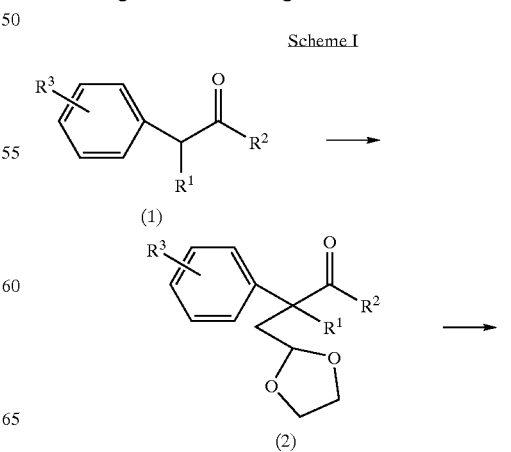

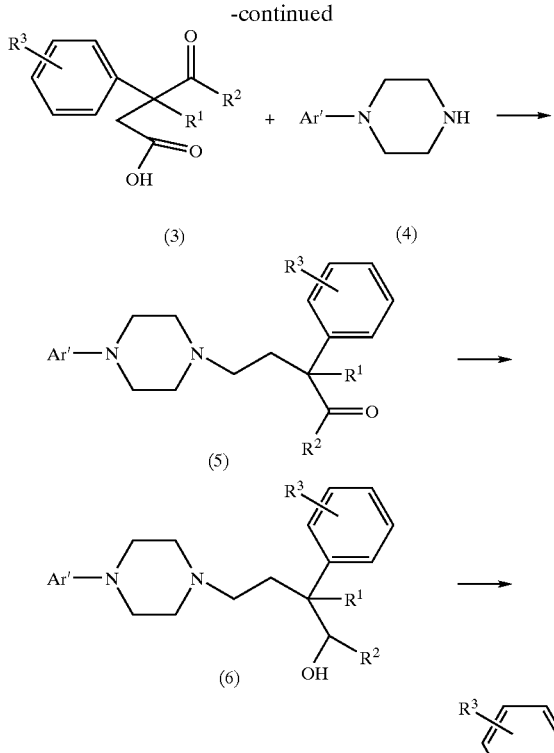

(3) (4) (5) (6) (7)

Starting material (1) is treated with a base, preferably potassium tert-butoxide, followed by alkylation with 2-bromomethyl-1,3-dioxolane. Other appropriate bases include sodium hydride, sodium hydroxide, potassium hydroxide, potassium carbonate, cesium carbonate and the like.

The reaction is preferably conducted in a solvent such as dimethyl sulfoxide at a temperature of 15° C. to reflux, with a temperature of 45–55° C. being most preferred, and is substantially complete in 1 to 24 hours to prepare intermediate (2).

Treatment of (2) with an acid, such as hydrochloric acid or p-toluene-sulfonic acid in a suitable organic solvent, achieves aldehyde (3). Generally, the reaction is conducted in a protic solvent, such a mixture of aqueous acid and acetone, at temperatures of from about 5° to 75° C., preferably at ambient temperature.

Aldehyde (3) is coupled with the desired aryl piperidine (4) by reductive amination to prepare (5). The reaction is preferably conducted at ambient temperature in a non-reactive solvent such as dichloroethane or methylene chloride in the presence of sodium triacetoxyborohydride and is substantially complete in one to 24 hours. See for example A. F. Abdel-Magid, et al., *J. Org. Chem.*, 61, 3849 (1996).

Reduction of (5) is readily accomplished using a reducing agent such as sodium borohydride or, preferably, diisobutylaluminum hydride to prepare the hydroxy compound (6). The reaction is preferably conducted in an organic solvent such as methylene chloride at temperatures of from about −20° C. to 0° C.

Further reduction of (6) to achieve product (7) may be achieved by treatment with a reducing agent such as triethylsilane or boron trifluoride (when $R^2$ is phenyl or substituted phenyl) or by treatment with an acid, such as hydrochloric acid or trifluoroacetic acid, in an aprotic solvent such as tetrahydrofuran, at ambient temperature to form the double bond, followed by hydrogenation with, for example, hydrogen and palladium on carbon.

Starting material (1) is either commercially available or can be prepared by coupling (8) [See Nahm and Weinreb, *Tetrahedron Lett.*, 22, 3815, (1981)] and (9) as described in Scheme II, below.

Scheme II

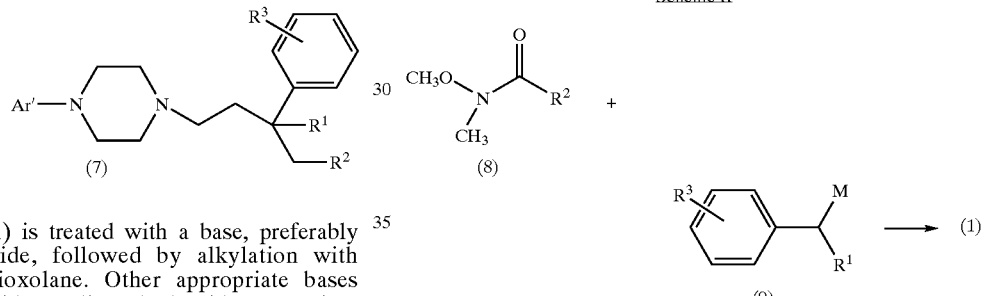

(8) (9)

M is a metallic salt, such as lithium or magnesium halide. The reaction is preferably conducted under an inert atmosphere preferably nitrogen, in an aprotic solvent, such as tetrahydrofuran, at ambient temperatures.

More specifically, the compounds of formula Ia can be prepared following the procedure described in Scheme III. All substituents, unless otherwise indicated, are previously defined. The reagents and starting materials are readily available to one of ordinary skill in the art.

Scheme III

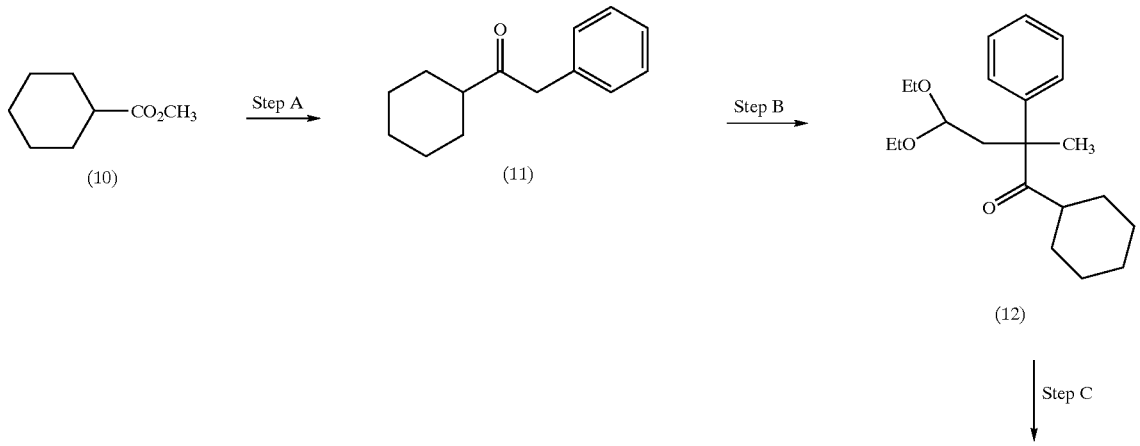

(10) Step A (11) Step B (12)

Step C

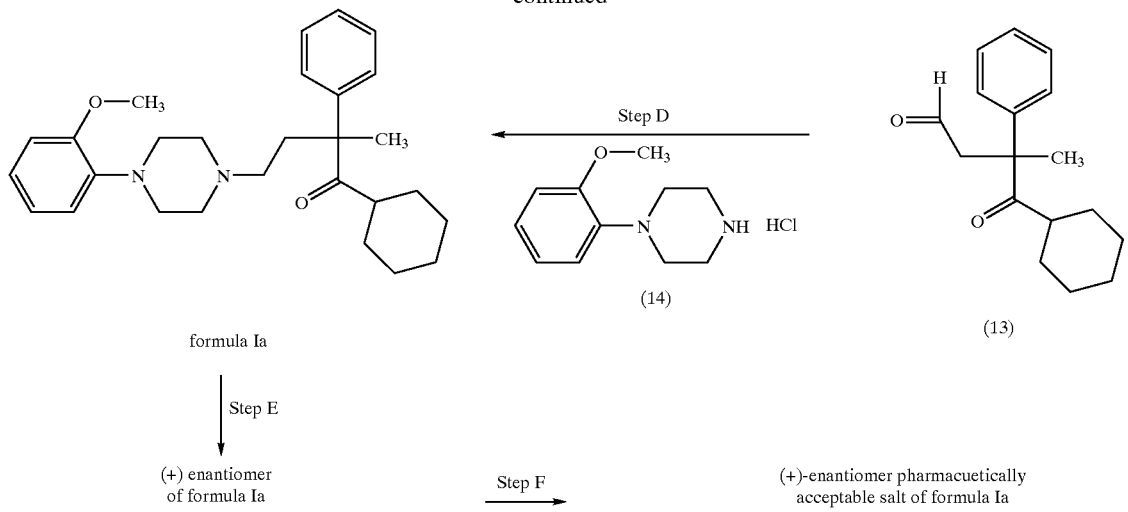

formula Ia

Step E (+) enantiomer of formula Ia

Step F (14)

(13)

(+)-enantiomer pharmacuetically acceptable salt of formula Ia

In Scheme III, step A, the ester of structure (10) is treated with benzylmagnesium chloride or benzylmagnesium bromide under standard conditions well known in the art to provide the ketone of structure (11). For example, about 1.05 to about 1.1 equivalents of a suitable amine, such as dimethylamine is dissolved in a suitable organic solvent, such as tetrahydrofuran (cooled to about −5° C.) under an inert atmosphere. The solution is warmed to room temperature and 1.0 equivalents of the ester (10) are added with stirring. Then approximately 1.0 to 1.05 equivalents of benzylmagnesium chloride is slowly added to the solution, maintaining the temperature at about 15–20° C. with a cooling bath during the addition. After addition is complete, the reaction is stirred at room temperature for about 1 to 2 hours, then cooled to less than 0° C. and then carefully quenched with a suitable acid, such as HCl. The quenched reaction is then extracted with a suitable organic solvent, such as tert-butyl methyl ether (hereinafter referred to as MTBE), the organic layers are combined, dried over anhydrous magnesium sulfate, filtered and concentrated to provide ketone (11). Ketone (11) can be purified by techniques well known in the art, such as flash chromatography on silica gel with a suitable eluent, such as ethyl acetate/hexane to provide the purified material. Alternatively, the crude ketone (11) can be carried on to step B.

In Scheme III, step B, ketone (11) is alkylated with bromoacetaldehyde diethyl acetal, and then iodomethane, under conditions well known in the art to provide compound of structure (12). For example, ketone (11) is dissolved in a suitable organic solvent, such as methyl sulfoxide and treated with about 1.05 to about 1.1 equivalents of a suitable base, such as potassium tert-butoxide. The reaction is stirred for about 15 to 30 minutes and about 1.0 to about 1.05 equivalents of bromoacetaldehyde diethyl acetal is added dropwise to the reaction. One of ordinary skill in the art would readily appreciate that bromoacetaldehyde dimethyl acetal, bromoacetaldehyde ethylene acetal and the like may be used in place of the corresponding diethyl acetal. The reaction mixture is then heated to about 50° C. for about 2 to 2.5 hours. The reaction mixture is then cooled with an ice/water bath and about 2.2 equivalents of a suitable base, such as potassium tert-butoxide is added. The reaction is allowed to stir for about 15 to 30 minutes with continued cooling and then about 1.5 to about 1.8 equivalents of iodomethane is added dropwise to the reaction mixture keeping the temperature of the mixture below 41° C., preferably below 21° C. After addition is complete, the reaction is warmed to room temperature and stirred for about 1 to 4 hours. The reaction mixture is then partitioned between water and a suitable organic solvent, such as MTBE. The layers are separated and the organic phase is washed with water, brine, dried over anhydrous magnesium sulfate, filtered and concentrated under vacuum to provide the compound (12).

In Scheme III, step C, compound (12) is hydrolyzed under acidic conditions to provide aldehyde (13) in a manner analogous to the procedure described in Scheme I. More specifically, for example, compound (12) is dissolved in a suitable organic solvent, such as acetone and treated with a suitable acid, such as hydrochloric acid. The reaction mixture is stirred for about 1 to 3 hours at room temperature. The reaction mixture is then extracted with a suitable organic solvent, such as ethyl acetate or methylene chloride, the organic extracts are combined, washed with brine, dried over anhydrous magnesium sulfate, filtered and concentrated under vacuum to provide aldehyde (13). Aldehyde (13) can be purified by techniques well known in the art, such as flash chromatography on silica gel with a suitable eluent, such as ethyl acetate/hexane. Alternatively, crude aldehyde (13) can be used directly in step D.

In Scheme III, step D, aldehyde (13) is reductively aminated, under conditions well known in the art, with piperazine (14) to provide the compound of formula Ia in a manner analogous to the procedure described in Scheme I. More specifically, for example, aldehyde (13) is dissolved in a suitable organic solvent, such as methylene chloride. To this solution is added about 1.1 equivalents of piperazine (14). Acetic acid may optionally be added to aid in dissolution of the piperazine (14). Then about 1.2 to 1.3 equivalents of sodium triacetoxyborohydride is added and the reaction is stirred at room temperature for about 3 to 5 hours. The reaction is then quenched by addition of a suitable base, such as aqueous sodium hydroxide to provide a pH of about 10 to about 12. The quenched reaction is then extracted with a suitable organic solvent, such as methylene chloride. The organic extracts are combined, washed with brine, dried over anhydrous magnesium sulfate, filtered and concentrated under vacuum to provide the compound of formula Ia. This material can then be purified by techniques well known in the art, such as flash chromatography on silica gel with a suitable eluent, such as ethyl acetate/hexane.

The free base of formula Ia can be converted to the corresponding pharmaceutically acceptable salts under standard conditions well known in the art. For example, the free base of formula Ia is dissolved in a suitable organic solvent, such as methanol, treated with one equivalent of maleic or oxalic acid for example, or two equivalents of hydrochloric acid for example, and then concentrated under vacuum to provide the corresponding pharmaceutically acceptable salt. The residue can then be purified by recrystallization from a suitable organic solvent or organic solvent mixture, such as methanol/diethyl ether.

In Scheme III, step E, the (+) enantiomer of formula Ia can be separated from the (−) enantiomer using techniques and procedures well known in the art, such as that described by J. Jacques, et al., "Enantiomers, Racemates, and Resolutions", John Wiley and Sons, Inc., 1981. For example, chiral chromatography with a suitable organic solvent, such as ethanol/acetonitrile and Chiralpak AD packing, 20 micron can also be utilized to effect separation of the enantiomers.

In Scheme III, step F, the (+) enantiomer of formula Ia is converted to its pharmaceutically acceptable salt, such as the monohydrochloride, dihydrochloride, monohydrobromide, dihydrobromide, formula Ia/succinate(1:1), formula Ia/succinate 2:1, phosphate, d-tartrate, 1-tartrate or maleate salt, in a manner analogous to the procedure described at the end of step D above.

Alternatively, compounds of structure (5) can be prepared following the procedure described in Scheme IV. All substituents, unless otherwise indicated, are previously defined. The reagents and starting materials are readily available to one of ordinary skill in the art.

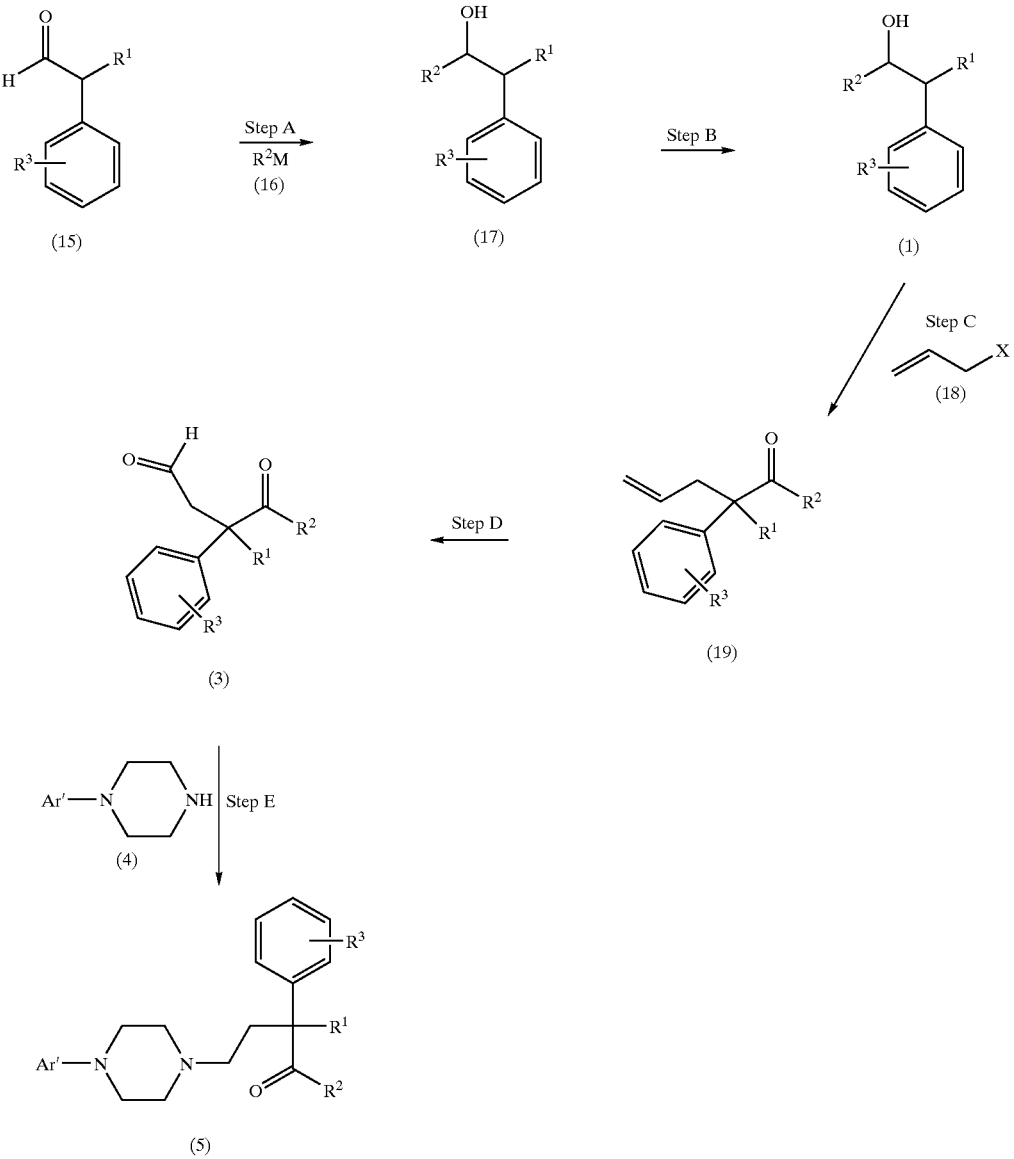

In Scheme IV, step A, aldehyde (15) is combined with a suitable organometallic reagent (16) under conditions well known in the art to provide alcohol (17). Examples of suitable organometallic reagents include Grignard Reagents, alkyl lithium reagents, alkyl zinc reagents, and the like.

Grignard Reagents are preferred. For examples of typical Grignard Reagents and reaction conditions, see J. March, "Advanced Organic Chemistry: Reactions, Mechanisms, and Structure", $2^{nd}$ Edition, McGraw-Hill, pages 836–841 (1977). More specifically, aldehyde (15) is dissolved in a suitable organic solvent, such as tetrahydrofuran or toluene, cooled to about −5° C. and treated with about 1.1 to 1.2 equivalents of a Grignard reagent of formula (16) wherein M is MgCl or MgBr. The reaction is allowed to stir for about 0.5 to 2 hours, then quenched, and alcohol (17) is isolated. For example, the reaction mixture is poured onto ice-cold 1N HCl, the quenched mixture is extracted with a suitable organic solvent, such as toluene, the organic extracts are dried either azeotropically or over a suitable drying agent, such as anhydrous magnesium sulfate, filtered and concentrated under vacuum to provide alcohol (17).

In Scheme IV, step B, alcohol (17) is oxidized under standard conditions well know in the art, such as those described by J. March, "Advanced Organic Chemistry: Reactions, Mechanisms, and Structure", $2^{nd}$ Edition, McGraw-Hill, pages 1082–1084 (1977), to provide ketone (1). [Ketone (1) is the starting material used in Scheme I above.]

For example, alcohol (17) is dissolved in a suitable organic solvent, such as methylene chloride, the solution cooled with a wet ice-acetone bath, and treated with 2.5 to 3.0 equivalents of dimethyl sulfoxide. After stirring for about 30 minutes, the reaction is then treated with about 1.8 equivalents of $P_2O_5$. The reaction is allowed to stir for about 3 hours and then, preferably, treated over about 30 minutes with about 3.5 equivalents of a suitable amine, such as triethylamine. The cooling bath is then removed and the reaction is allowed to stir for about 8 to 16 hours. The ketone (1) is then isolated by standard extraction techniques well known in the art. The above oxidation is also performed using standard Swern Oxidation conditions which are well known to one of ordinary skill in the art.

In Scheme IV, step C, ketone (1) is treated with a suitable base followed by addition of the alkene (18), wherein X is a suitable leaving group, to provide compound (19). For example, ketone (1) is combined with an excess of alkene (18) in a suitable organic solvent, such as tetrahydrofuran, and cooled with a wet ice acetone bath. Examples of suitable leaving groups are Cl, Br, I, tosylate, mesylate, and the like. Preferred leaving groups are Cl and Br. About 1.1 equivalents of a suitable base is added and the reaction is allowed to stir for about 2 hours at room temperature. Examples of suitable bases are potassium tert-butoxide, sodium hydride, $NaN(Si(CH_3)_3)_2$, LDA, $KN(Si(CH_3)_3)_2$, $NaNH_2$, sodium ethoxide, sodium methoxide and the like. Potassium tert-butoxide is the preferred suitable base. The reaction is then quenched with aqueous acid and compound (19) is isolated by extraction with a suitable organic solvent, such as heptane. The heptane extracts are washed with sodium bicarbonate, dried over anhydrous magnesium sulfate, filtered and concentrated under vacuum to provide compound (19).

In Scheme IV, step D, compound (19) is treated with a suitable oxidizing agent to provide aldehyde (3). [Aldehyde (3) is also prepared in Scheme I.] Examples of suitable oxidizing agents are ozone, $NaIO_4$/Osmium catalyst, and the like. Ozone is the preferred oxidizing agent. Examples of suitable oxidizing reagents and conditions are described by J. March, "Advanced Organic Chemistry: Reactions, Mechanisms, and Structure", $2^{nd}$ Edition, McGraw-Hill, pages 1090–1096 (1977).

For example, compound (19) is dissolved in a suitable organic solvent, such as methanol, a small amount of Sudan III is added, and the solution is cooled to about −20° C. Ozone is bubbled into the solution for about 4 hours until the pink color turns to a pale yellow color. Then $Me_2S$ is added to the reaction mixture and the cooling bath is removed. Concentration of the reaction mixture under vacuum provides the intermediate dimethyl acetal of aldehyde (3). This dimethyl acetal is readily hydrolyzed under standard acidic conditions to provide aldehyde (3). Alternatively, direct acidic work-up of the crude reaction mixture provides aldehyde (3). Alternatively, aldehyde (3) can be obtained directly by ozonolysis of (19) in a non-acetal forming solvent, such as methylene chloride.

In Scheme IV, step E, aldehyde (3) is reductively aminated under conditions analogous to those described above in Scheme III, step D, to provide compound (5). [Compound 5 is also prepared in Scheme I.]

Scheme V provides an alternative synthesis for the preparation of compound (5). All substituents, unless otherwise indicated, are previously defined. The reagents and starting materials are readily available to one of ordinary skill in the art.

Scheme V

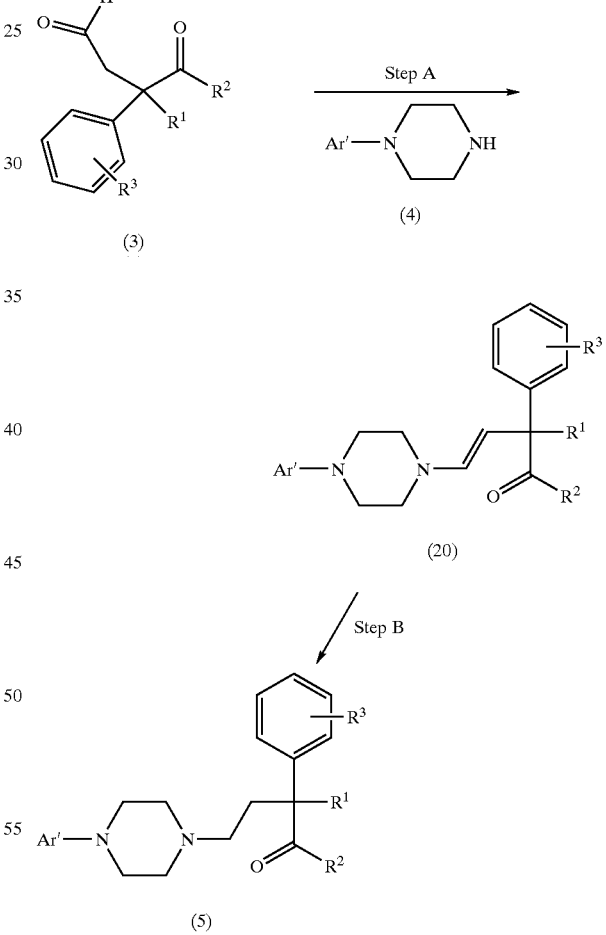

In Scheme V, step A, aldehyde (3) is condensed with piperidine (4) under standard conditions well known in the art to provide the enamine (20). For example, about 1.05 equivalents of aldehyde (3) dissolved in a suitable organic solvent, such as isopropyl acetate or isopropanol, is added to neat piperazine (4), free base. Additional organic solvent is added to produce a slurry and the reaction is stirred for about 1 to 2 hours. The enamine (20) is then isolated by standard techniques, such as collection by filtration.

In Scheme V, step B, the enamine (20) is hydrogenated under conditions well known by one of ordinary skill in the art to provide compound (5). For example, enamine (20) is combined with a suitable organic solvent, such as isopropyl alcohol and a catalytic amount of 5% palladium on carbon in a Parr bottle. The mixture is placed under 50 psi of hydrogen and shaken for about 2 days at room temperature. The slurry is then filtered to remove catalyst and the filtrate is concentrated to provide compound (5).

The following examples represent typical syntheses of the compounds of Formula I and formula Ia as described generally above. These examples are illustrative only and are not intended to limit the invention in any way. The reagents and starting materials are readily available to one of ordinary skill in the art. As used herein, the following terms have the meanings indicated: "aq" refers to aqueous; "eq" refers to equivalents; logic refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ"refers to part per million down-field from tetramethylsilane; "THF" refers to tetrahydrofuran; "DMF" refers to N,N-dimethylformamide; "IPA" refers to isopropyl alcohol; "iPrOAc" refers to isopropyl acetate; "AcOH" refers to acetic acid; "HRMS" refers to high resolution mass spectrometry; "$Et_3N$" refers to triethylamine; "LDA" refers to lithium diisopropyl amide; "RT" refers to room temperature; "SRI" refers to serotonin reuptake inhibitor; "aq" refers to aqueous; and "MTBE" refers to tert-butyl methyl ether.

EXAMPLE 1

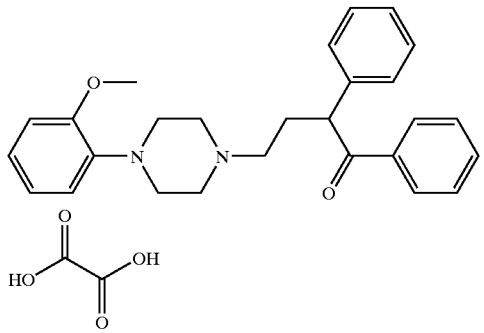

1-(2-methoxyphenyl)-4-[3-(benzoyl)-3-(phenyl)propyl]piperazine oxalate

A. Preparation of 2-(2'-benzoyl-2'-phenyl)ethyl-1,3-dioxolane

To a stirred suspension of sodium hydride (61.25 mmol) in 150 mL of dimethylformamide at 0° C. under nitrogen was added dropwise a solution of deoxybenzoin (50.96 mmol) in 150 mL of tetrahydrofuran. The mixture was stirred at 0° C. for 1 hour and room temperature for 1 hour. To the mixture 2-bromomethyl-1,3-dioxolane (60.55 mmol) and catalyst potassium iodide (6.0 mmol) were added. The mixture was heated to reflux for 13 hours. After cooling, diethyl ether (300 mL) and water (300 mL) were added. The organic layer was separated and washed with water (150 mL×2). Purification by flash chromatography using hexanes and ethyl acetate gave 2-(2'-benzoyl-2'-phenyl)ethyl-1,3-dioxolane (8.18 g; 57%).

B. Preparation of 3-benzoyl-3-phenylpropionaldehyde

To 100 mL of acetone was added 2-(2'-benzoyl-2'-phenyl)ethyl-1,3-dioxolane (8.85 mmol) and 100 mL of 2N hydrochloric acid solution. After the mixture was stirred at room temperature for 7 hours, 100 mL of 2N sodium hydroxide was added. Acetone was evaporated and the residue was extracted with diethyl ether and hexanes (1:1, 100 mL×3). The combined organic layer was dried (sodium sulfate), filtered and concentrated. The residue was found to be rather pure material (3-benzoyl-3-phenylpropionaldehyde) and therefore used for next step.

C. Preparation of 1-(2-methoxyphenyl)-4-[3-(benzoyl)-3-(phenyl)propyl]piperazine The 3-benzoyl-3-phenylpropionaldehyde residue obtained from Step B, above, (~8.85 mmol) was dissolved in 110 mL of methylene chloride. To this solution was added 2-methoxyphenylpiperazine (10.61 mmol) and sodium triacetoxyboranehydride, $NaBH(OAc)_3$, (10.61 mmol). The mixture was stirred at room temperature for 3 hours. Aqueous workup followed by flash chromatography gave pure product 1-(2-methoxyphenyl)-4-[3-(benzoyl)-3-(phenyl)propyl]piperazine (3.48 g) in 95% yield for last two steps. One equivalent of oxalic acid was added to the free base dissolved in methanol. The solvent was evaporated and the product was dried under vacuum to form the oxalate salt.

m.p.=161–163° C.; MS (m/e): 414 ($M^+$).

EXAMPLE 2

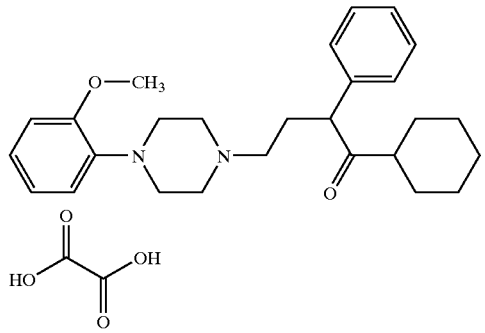

1-(2-methoxyphenyl)-4-[3-(cyclohexanecarbonyl)-3-(phenyl)propyl]piperazine oxalate A. Preparation of cyclohexyl benzyl ketone To a stirred solution of N-methyl-N-methoxy cyclohexanecarboxamide (7.42 mmol) in 30 mL of tetrahydrofuran at 0° C. under nitrogen was added a solution of benzyl magnesium chloride (2.0 M in tetrahydrofuran, 4.5 mL, 9.0 mmol). The mixture was stirred at 0° C. for 30 minutes and at room temperature for 1 hour. Diethyl ether (50 mL) and water (20 mL) were added. The organic layer was separated, dried, filtered, and concentrated. Purification of the residue by flash chromatography using hexanes and ethyl acetate gave cyclohexyl benzyl ketone (1.05 g) in 70% yield as oil.

B. Preparation of 2-(2'-cyclohexanecarbonyl-2'-phenyl)ethyl-1,3-dioxolane

Following the procedures described in the Example 1, Step A, the reaction of cyclohexyl benzyl ketone (5.09 mmol) and 2-bromomethyl-1,3-dioxolane (7.63 mmol) in the presence of sodium hydride (5.60 mmol) gave 2-(2'-cyclohexanecarbonyl-2'-phenyl)ethyl-1,3-dioxolane (0.86 g) in 59% yield.

C. Preparation of 3-cyclohexanecarbonyl-3-phenylpropionaldehyde

Following the procedures described in the Example 1, Step B, the reaction of 2-(2'-cyclohexanecarbonyl-2'-phenyl)ethyl-1,3-dioxolane (2.98 mmol) with 1N hydrochloric acid gave 3-cyclohexanecarbonyl-3-phenylpropionaldehyde as a crude product in 100% yield.

D. Preparation of 1-(2-methoxyphenyl)-4-[3-(cyclohexanecarbonyl)-3-(phenyl)propyl]piperazine Following the procedures described in the Example 1, Step C, the reaction of 3-cyclohexanecarbonyl-3-phenylpropionaldehyde (1.39 mmol) and 2-methoxyphenylpiperazine (1.39 mmol) with sodium triacetoxyboranehydride (1.80 mmol) gave pure product 1-(2-methoxyphenyl)-4-[3-(cyclohexanecarbonyl)-3-(phenyl)propyl]piperazine (464 mg) in 79% yield. The oxalate salt was prepared as described above.

m.p.=149–151° C.; MS (m/e): 420 (M$^+$).

EXAMPLE 3

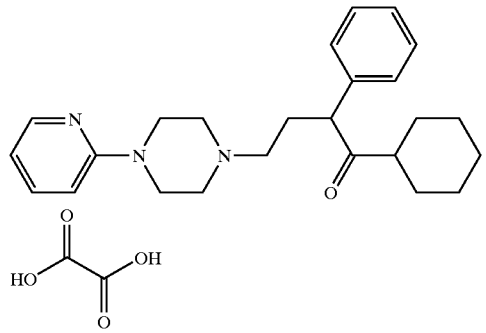

1-(2-pyridyl)-4-[3-(cyclohexanecarbonyl)-3-(phenyl)propyl]piperazine oxalate

Following the procedures described in the Example 1, Step C, the reaction of 3-cyclohexanecarbonyl-3-phenylpropionaldehyde (1.55 mmol) and 1-(2-pyridyl)piperazine (1.55 mmol) with sodium triacetoxyboranehydride (2.0 mmol) gave pure product 1-(2-pyridyl)-4-[3-(cyclohexanecarbonyl)-3-(phenyl)propyl]piperazine (475 mg) in 78% yield. The oxalate salt was prepared as described above.

m.p.=185–187° C.; MS (m/e): 391 (M$^+$).

EXAMPLE 4

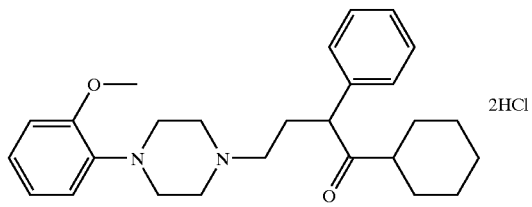

1-(2-ethoxyphenyl)-4-[3-(cyclohexanecarbonyl)-3-(phenyl)propyl]piperazine dihydrochloride Following the procedures described in the Example 1, Step C, the reaction of 3-cyclohexanecarbonyl-3-phenylpropionaldehyde (1.02 mmol) and 1-(2-ethoxyphenyl)piperazine (1.13 mmol) with sodium triacetoxyboranehydride (1.33 mmol) gave pure product 1-(2ethoxyphenyl)-4-[3-(cyclohexanecarbonyl)-3-(phenyl)propyl]piperazine (270 mg) in 52% yield. To a solution of free base in methanol was added required amount of hydrochloric acid solution in diethyl ether. The solvents were removed by reduced pressure, and the product was dried under vacuum to give dihydrochloric acid salt.

m.p.=180–183° C.; MS (m/e): 434 (M$^+$).

EXAMPLE 5

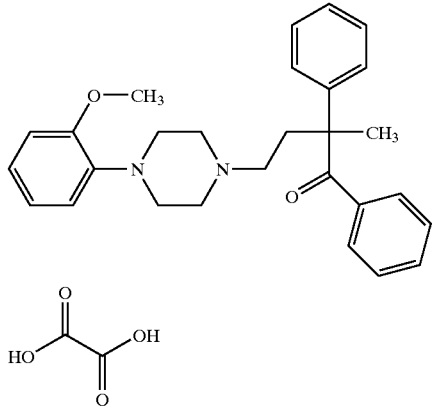

1-(2-methoxyphenyl)-4-[3-(benzoyl)-3-(phenyl)butyl]piperazine oxalate

A. Preparation of 2-(2'-benzoyl-2'-phenyl)propyl-1,3-dioxolane

Following the procedures described in the Example 1, Step A, the reaction of 2-(2'-benzoyl-2'-phenyl)ethyl-1,3-dioxolane (3.54 mmol) and iodomethane (10.62 mmol) in the presence of sodium hydride (4.25 mmol) gave 2-(2'-benzoyl-2'-phenyl)propyl-1,3-dioxolane (0.60 g).

B. Preparation of 3-benzoyl-3-phenylbutyraldehyde

Following the procedures described in the Example 1, Step B, the reaction of 2-(2'-benzoyl-2'-phenyl)propyl-1,3-dioxolane (0.60 g) with 3N hydrochloric acid gave 3-benzoyl-3-phenylbutyraldehyde as a crude product (0.32 g).

C. Preparation of 1-(2-methoxyphenyl)-4-[3-(benzoyl)-3-(phenyl)butyl]piperazine Following the procedures described in the Example 1, Step C, the reaction of 3-benzoyl-3-phenylbutyraldehyde (0.32 g) and 1-(2-methoxyphenyl)piperazine (0.23 g) with sodium triacetoxyboranehydride (0.33 g) gave pure product 1-(2-methoxyphenyl)-4-[3-(benzoyl)-3-(phenyl)butyl]piperazine (0.12 g). The oxalate salt was prepared as described above.

m.p.=192–193° C.; MS (m/e): 428 (M+).

EXAMPLE 6

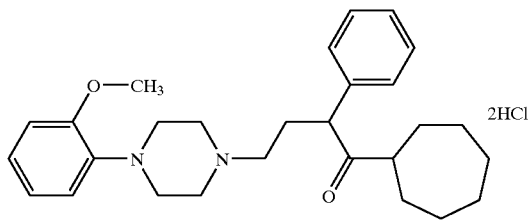

1-(2-methoxyphenyl)-4-[3-(cycloheptanecarbonyl)-3-(phenyl)propyl]piperazine dihydrochloride Following the procedures described in the Example 1, Step C, the reaction of 3-cycloheptanecarbonyl-3-phenylpropionaldehyde (2.52 mmol) and 1-(2-methoxyphenyl)piperazine (2.52 mmol) with sodium triacetoxyboranehydride (3.28 mmol) gave pure product 1-(2-methoxyphenyl)-4-[3-(cycloheptanecarbonyl)-3-(phenyl)propyl]piperazine (770 mg) in 70% yield. The dihydrochloric acid salt was prepared as described above.

m.p.=193–194° C.; MS (m/e): 434 (M+).

EXAMPLE 7

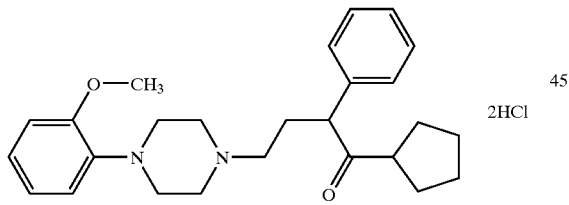

1-(2-methoxyphenyl)-4-[3-(cyclopentanecarbonyl)-3-(phenyl)propyl]piperazine dihydrochloride Following the procedures described in the Example 1, Step C, the reaction of 3-cyclopentanecarbonyl-3-phenylpropionaldehyde (1.36 mmol) and 1-(2-methoxyphenyl)piperazine (1.49 mmol) with sodium triacetoxyboranehydride (1.77 mmol) gave pure product 1-(2-methoxyphenyl)-4-[3-(cyclopentanecarbonyl)-3-(phenyl)propyl]piperazine (370 mg) in 67% yield. The dihydrochloric acid salt was prepared as described above.

m.p.=210–212° C.; MS (m/e): 406 (M+).

EXAMPLE 8

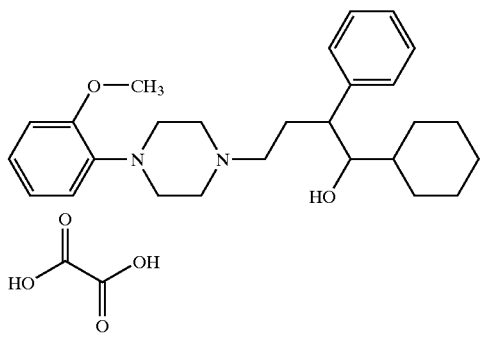

1-(2-methoxyphenyl)-4-[4-(cyclohexyl)-4-(hydroxy)-3-(phenyl)butyl]piperazine oxalate To a stirred solution of 1-(2-methoxyphenyl)-4-[3-(cyclohexanecarbonyl)-3-(phenyl)propyl]piperazine (0.11 g, 0.20 mmol) in methylene chloride (10 mL) at −78° C. under nitrogen was added Dibal-H™ solution (0.89 mmol). The mixture was stirred at −78° C. for 1 hour and then slowly warmed to room temperature for 16 hours. Workup followed by purification by flash chromatography gave pure 1-(2-methoxyphenyl)-4-[4-(cyclohexyl)-4-(hydroxy)-3-(phenyl)butyl]piperazine (0.086 g) in 78% yield. The oxalate salt was prepared as described above.

m.p.=100–102° C.; MS (m/e): 422 (M+).

EXAMPLE 9

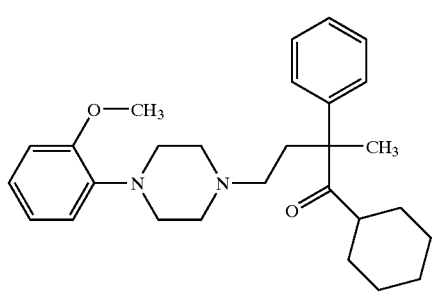

1-(2-methoxyphenyl)-4-[3-(cyclohexanecarbonyl)-3-(phenyl)butyl]piperazine

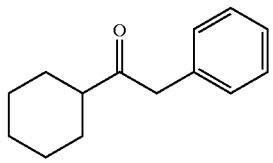

Preparation of 2-phenyl-1-cyclohexane-ethan-1-one

Scheme III, step A: A 5 L reaction vessel was charged with tetrahydrofuran (1.05 L) under an atmosphere of nitrogen. The solution was cooled with an acetone/ice bath to about −5° C. Liquid dimethylamine (115.9 g, 2.57 mol) was then added through a teflon addition tube. The cooling bath was removed and the solution was allowed to warm to about 15–20° C. Methyl cyclohexanecarboxylate (341.7 g, 2.40 mol) was then added resulting in a tea-colored solution.

Then benzylmagnesium chloride (2.52 L of a 2.0 M solution in THF, 246 mol) was slowly added at a rate to complete addition in about 1.8 to about 2.2 hours. A cooling bath was applied to maintain the temperature of the reaction mixture at about 15–20° C. during the addition. After the benzylmagnesium chloride solution was added, the resulting slurry was stirred at room temperature for about 1–2 hours. The reaction mixture was then cooled to less than 0° C. Concentrated HCl (709.7 g, 7.2 mol) was combined with water (3.08 L) and the solution was cooled to less than 5° C. The dilute acid mixture was added to a 22 L reaction vessel with an ice bath applied to the vessel. The above-chilled reaction mixture was then slowly poured into the chilled dilute acid solution with stirring. An extreme exotherm occurs (Use Caution!). Addition rate of the reaction mixture should be controlled to maintain the temperature of the quench solution below 45° C. After addition of the reaction mixture to the dilute acid solution, the quenched reaction mixture was cooled to room temperature and the pH was adjusted to about 6.5 to 7.5 with a sufficient amount of concentrated HCl. The quenched reaction mixture was extracted with MTBE (1.71 L). The layers were separated and the organic layer was washed with a water/MTBE mixture (1.03 L/1.37 L) followed by a second washing with a water/MTBE mixture (1.03 L/1.03 L). The organic layers were combined, washed with brine (683 mL), dried over anhydrous magnesium sulfate (167 g), filtered and concentrated under vacuum. The crude oil was dried under house vacuum for 5–16 hours to provide crude 2-phenyl-1-cyclohexane-ethan-1-one (522.3 g). This crude material was used in the next reaction without further purification.

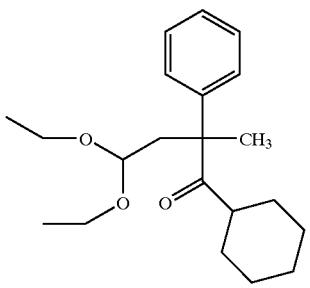

Preparation of 1,1-diethoxy-3-phenyl-3-cyclohexanecarbonylbutane

Scheme III, step B; 2-Phenyl-1-cyclohexane-ethan-1-one (8.26 g, 40.8 mmol) was combined with DMSO (45 mL) in a 3-necked, 250 mL round bottom flask equipped with a magnetic stir bar, thermocouple-digital thermometer unit and an addition funnel. To the stirring solution was added potassium tert-butoxide (5.04 g, 44.9 mmol). A 16° C. exotherm was observed and the yellow solution became dark brown. The reaction mixture was stirred for an additional 15 minutes after addition was complete, and then bromoacetaldehyde diethyl acetal (8.26 g, 41.9 mmol) was added dropwise via the addition funnel over approximately 10 minutes. The reaction mixture was then heated at 50° C. for 2 to 2.5 hours during which the reaction mixture became yellow. The reaction mixture was then cooled with an ice/water bath to about 9.5° C. and potassium tert-butoxide (10.07 g, 89.7 mmol) was added resulting in an exothermic reaction and change in color from yellow to brown with the cooling bath still in place, the reaction mixture was stirred for an additional 15 minutes followed by dropwise addition of iodomethane (10.26 g, 72.3 mmol, neat). The temperature of the reaction mixture was maintained at or below 21° C. Any exotherm during the iodomethane addition should be maintained below 41–43° C., which is the boiling point of iodomethane. After addition was complete, the reaction mixture was allowed to stir for 1 to 4 hours at room temperature. The reaction mixture was then partitioned between MTBE (100 mL) and water (100 mL). The organic phase was washed with water (3×50 mL), brine (50 mL), dried over anhydrous magnesium sulfate, suction filtered and concentrated under vacuum to provide crude 1,1-diethoxy-3-phenyl-3-cyclohexanecarbonyl-butane (13.6 g) as a yellow oil. This crude material was used in the next reaction without further purification.

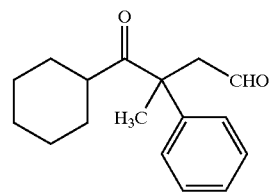

Preparation of 1-cyclohexyl-2-phenyl-butan-1-one-4-al

Scheme III, step C; 1,1-Diethoxy-3-phenyl-3-cyclohexanecarbonyl-butane (74.4 g, 224 mmol) was dissolved in acetone (800 mL) followed by addition of 3.0 N HCl (800 mL). The reaction mixture was stirred for one hour at room temperature. It was then concentrated under vacuum to less than ½ its original volume and then extracted with methylene chloride (800 mL). The organic extract was then washed with brine (300 mL), dried over anhydrous magnesium sulfate, suction filtered and concentrated under vacuum to provide crude 3-phenyl-3-cyclohexanecarbonyl-butan-1-al (57.8 g). Alternatively, the dried and filtered methylene chloride solution can be used directly in the next step without concentration.

Preparation of the final title compound, 1-(2-methoxyphenyl)-4-[3-(cyclohexanecarbonyl)-3-(phenyl)butyl]piperazine Scheme III, step D; 3-Phenyl-3-cyclohexanecarbonylbutan-1-al (57.8 g, 224 mmol) was dissolved in methylene chloride (1650 mL) followed by addition of 1-(2-methoxyphenyl)piperazine hydrochloride (56.3 g, 246 mmol). Acetic acid (41 mL) may optionally be added to turn the slurry into a solution. To the stirred solution, sodium triacetoxyborohydride (60.3 g, 284 mmol) was slowly added. A slight exotherm resulted and a slurry was produced. The reaction mixture was stirred for an additional 3 hours at room temperature. The reaction was then quenched by addition of 2.0 N sodium hydroxide (1050 mL) producing a pH of about 10 for the quenched reaction mixture. The mixture was then extracted with methylene chloride (2 times, 1L and 300 mL) The organic extracts were combined, washed successively with 1.0 N HCl (600 mL), 1.0 N sodium hydroxide (600 mL), brine (600 mL), dried over anhydrous magnesium sulfate, filtered and concentrated under vacuum to provide the final title compound as a thick oil;

UV (MeOH): $\lambda_{max}$=243 nm, $\epsilon_{243}$=7110; $\lambda_{max}$=281 nm, $\epsilon_{281}$=3200 IR (CDCl$_3$, cm$^{-1}$) 2937, 2856, 2836, 1698, 1499, 1451, 1377, 1316, 1242, 1029 $^1$H NMR (300 MHz, DMSO) δ 7.75 (2H, m), 7.55 (2H, m), 6.93 (3H, m), 6.85 (2H, m), 3.75 (3H, s), 2.90 (4H, m), 2.43 (4H, m), 2.08 (5H, m), 1.5

(10H, m), 1.05 (3H, m) $^{13}$C NMR (300 MHz, DMSO) δ 214.18, 151.94, 141.25, 141.23, 128.45, 126.85, 126.74, 122.22, 120.79, 117.81, 111.97, 55.28, 54.54, 53.67, 53.13, 50.01, 45.30, 33.75, 30.44, 30.12, 25.21, 24.98, 24.93, 19.94. Anal. Calcd for $C_{28}H_{38}N_2O_2$: C, 77.38; H, 8.81; N, 6.45. Found: C, 76.44; H, 8.89; N, 6.01.

Preparation of 1-(2-methoxyphenyl)-4-[3-(cyclohexanecarbonyl)-3-(phenyl)butyl]piperazine maleate 1-(2-Methoxyphenyl)-4-[3-(cyclohexanecarbonyl)-3-(phenyl)butyl]piperazine (prepared directly above) was dissolved in warm methanol (50 mL) followed by addition of maleic acid (26.8 g) and MTBE (200 mL). This mixture was concentrated to a paste and then redissolved by addition of methanol (approximately 15 mL) and MTBE (200 mL). The mixture was seeded and an additional amount of MTBE (300 mL) was added once crystallization was initiated. The mixture was suction filtered, and the solid rinsed with MTBE and vacuum dried for 5 hours at 40° C. to provide the title compound (122 g).

In addition, one of ordinary skill in the art could prepare the title compound, 1-(2-methoxyphenyl)-4-[3-(cyclohexanecarbonyl)-3-(phenyl)butyl]piperazine, in a manner analogous to the procedures described above, from 3-cyclohexanecarbonyl-3-phenylbutyraldehyde and 1-(2-methoxyphenyl)piperazine as described generally in Scheme V.

Preparation of 1-(2-methoxyphenyl)-4-[3-(cyclohexanecarbonyl)-3-(phenyl)butyl]piperazine 2HCl The title compound is prepared by one of ordinary skill in the art, in a manner analogous to preparation of the above maleate salt, from the free base and hydrochloric acid to provide a white solid; mp (DSC)=192.81° C.

Preparation of (+)-1-(2-methoxyphenyl)-4-[3-(cyclohexanecarbonyl)-3-(phenyl)butyl]piperazine and (−)-1-(2-methoxyphenyl)-4-[3-(cyclohexanecarbonyl)-3-(phenyl)butyl]piperazine Scheme III, step E:
Materials:
Chiralpak AD Bulk packing, 20 micron
Acetonitrile
3A alcohol
Prochrom 8 cm column
Prochrom LC-80 system/collection system Column Preparation: A ProChem LC-80 automated system with an 8×19 cm Prochrom column (ProChem, 5622 West 73$^{rd}$ Street, Indianapolis, Ind. 46278) is slurry packed using approximately 500 g Chiralpak AD (Chiral Technologies, 730 Springdale Drive, Exton, Pa. 19341) in propanol (1 L). An eluent containing approximately 5% 3A alcohol in acetonitrile was prepared. Column flow rate was 155 mL/min and the detector was set at 280 nm. The racemic 1-(2-methoxyphenyl)-4-[3-(cyclohexanecarbonyl)-3-(methyl)-3-(phenyl)propyl]piperazine (25 g) was dissolved in acetonitrile (50 mL). Approximately 3 g of this solution was weighed into a flask and diluted with acetonitrile (50 mL). This solution was then pumped onto the column to begin separation of the (+) and (−) enantiomers of 1-(2-methoxyphenyl)-4-[3-(cyclohexanecarbonyl)-3-(phenyl) butyl]piperazine. Fractions were then collected with the (−) enantiomer eluting first. Approximate total cycle time is 15 minutes.

The enantiomeric excess of the two separated isomers was determined under the following conditions:

Column: 46×15 cm Chiralcel OH—H

Eluent: 3% ethanol in Heptane containing 0.2% dimethylamine

Flow rate: 0.6 mL/min

Temperature: ambient uv: 280 nm

% ee for the (−) enantiomer 96.4%.

% ee for the (+) enantiomer 96.6%.

Preparation of (+)-1-(2-methoxyphenyl)-4-[3-(cyclohexanecarbonyl)-3-(phenyl)butyl]piperazine dihydrochloride Scheme III, step F: (+)-1-(2-methoxyphenyl)-4-[3-(cyclohexanecarbonyl)-3-(phenyl)butyl]piperazine (15.0 g, 34.5 mmol, prepared above) was diluted with methanol (40 mL). To this solution was added HCl (9.58 g of a 26.3% solution in methanol, 69.0 mmol). The mixture began to form gelatinous-looking crystals and set up solid within minutes. To this mixture was added with vigorous stirring, diethyl ether (100 mL). The white solid was collected by suction filtration and then dried under vacuum at 45° C. for two days to provide the title compound (13.4 g, 76%) as a white solid; mp (DSC)=195.58° C.

IR (CDCl$_3$, cm$^{-1}$) 2976, 2939, 1700, 1502, 1462, 1451, 1267, 1243, 1021; $^1$H NMR (300 MHz, DMSO) δ 7.40 (2H, m), 73.1 (3H, m) 7.03 (3H, M) 6.90 (1H, m) 3.78 (3H, s) 3.49 (4H, m) 3.16 (5H, m) 2.64 (1H, m) 2.40 (3H, m) 1.56 (3H, s) 1.46 (4H, m) 1.11 (5H, m) 0.86 (1H, m); $^{13}$C NMR (300 MHz, DMSO) δ 213.46, 151.84, 139.56, 138.12, 128.72, 127.37, 126.86, 124.29, 120.85, 118.71, 112.29, 55.48, 54.06, 52.20, 50.78, 50.57, 46.93, 45.14, 30.31, 30.16, 25.15, 24.91, 24.89, 19.15; HRMS calcd for $C_{28}H_{39}N_2O_2$ (MH$^+$) 435.3012, found 435.3018. $[\alpha]^{25}_D$=+76.53° (c=1, MeOH), ee 99.3% (Chiral HPLC).

Preparation of (+)-1-(2-methoxyphenyl)-4-[3-(cyclohexanecarbonyl)-3-(phenyl)butyl]piperazine monohydrochloride Scheme III, step F: (+)-1-(2-methoxyphenyl)-4-[3-(cyclohexanecarbonyl)-3-(phenyl)butyl]piperazine (6.05 g, 13.9 mmol) was diluted with MTBE (120 mL) followed by addition of HCl (2.2 M solution in isopropanol, 6.3 mL, 13.9 mmol, prepared from 0.80 g of HCl gas in 10 mL of isopropanol). The mixture formed an oil/solid mixture which upon further stirring yielded a uniformly crystalline material. The mixture was suction-filtered and rinsed with MTBE to provide a white solid which was dried under vacuum at 45° C. (5.74 g, 96.2% ee).

(+)-1-(2-methoxyphenyl)-4-[3-(cyclohexanecarbonyl)-3-(phenyl)butyl]piperazine monohydrochloride can be prepared in an analogous manner as above from an equivalent of concentrated aqueous HCl in place of the gaseous HCl.

Alternative Preparation of 1-(2-methoxyphenyl)-4-[3-(cyclohexanecarbonyl)-3-(phenyl)butyl]piperazine

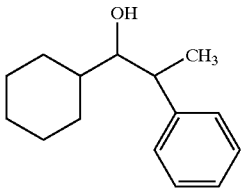

Preparation of 1-Cyclohexyl-2-phenylpropanol

Scheme IV, step A: To a solution of cyclohexylmagnesium chloride (50 mmol) in 25 mL of Et$_2$O and 40 mL of THF at −5° C. was added a solution of 2-phenylpropanaldehyde (5.36 g, 40 mmol) in 10 mL of THF. The reaction mixture exothermed to 5° C. After stirring at room temperature for 75 min, the solution was poured onto ice cold 1 N HCl, extracted with toluene, dried over MgSO$_4$, and concentrated to give the title compound as a colorless oil (6.15 g, 70%): $^1$H NMR (d$^6$-DMSO): δ 7.23–7.30 (m, 2H, phenyl CH), 7.15–7.22 (m, 3H, phenyl CH), 4.17–4.51 (br s, 1H, —OH), 3.23–3.33 (m, 1H, R$_2$C HOH), 2.78 (dq, J=7.0 Hz, J=7.1 Hz, 1H, —CH(CH$_3$)Ph), 1.23–1.83 (m, 6H, cyclohexyl CH), 1.20 (d, J=6.9 Hz, 3H, —CH(CH$_3$)Ph), 0.88–1.18 (m, 5H, cyclohexyl CH).

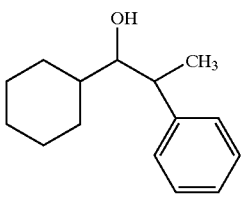

Preparation of Cyclohexyl 1-phenylethyl ketone

Scheme IV, step B: DMSO (118 mL, 1.6674 mol) was added dropwise to a solution of 126.42 g (0.579 mol) of 1-cyclohexyl-2-phenylpropanol in 1737 mL of CH$_2$Cl$_2$ (cooled in a wet ice acetone bath). After 29 min, 147.93 g (1.0422 mol) of P$_2$O$_5$ was added. After 11 min, the cooling bath was removed. An aliquot quenched with Et$_3$N showed complete reaction within 3 h at RT. The reaction mixture was cooled in a wet ice acetone bath. Et$_3$N (282 mL, 2.0265 mol) was added dropwise to the cooled reaction mixture over a 30 min period. The cooling bath was removed and the mixture was stirred overnight at RT. The reaction mixture was quenched by dropwise addition of 500 mL of 3 N HCl (aq) (pH=0). After shaking in separatory funnel, the aqueous phase was removed. The organic phase was washed with 500 mL of 3 N HCl (aq) (pH=0), washed twice with 1 L of 10% K$_2$CO$_3$ (aq) (pH=12;12), washed three times with 500 mL of NaOCl (aq) solution, washed with 1L of water, washed with 1 L of 25% NaCl (aq), dried over MgSO$_4$, gravity filtered and concentrated under vacuum with dry ice trap to collect Me$_2$S. An amber oil of the title compound (107.01 g, 85.437%) was obtained;
$^1$H NMR (d$^6$-DMSO) δ 7.30–7.37 (m, 2H, phenyl CH), 7.21–7.28 (m, 3H, phenyl CH), 4.08 (q, J=6.9 Hz, 1H, —CH(CH$_3$)Ph), 2.40–2.49 (m, 1H, cyclohexyl CH), 1.82–1.84 (m, 1H, cyclohexyl —CH$_2$), 1.67–1.69 (m, 1H, cyclohexyl —CH$_2$), 1.52–1.63 (m, 1H, cyclohexyl —CH$_2$), 1.34–1.43 (m, 1H, cyclohexyl —CH$_2$), 1.26 (d, J=6.9 Hz, 3H, —CH(CH$_3$)Ph), 1.01–1.24 (m, 4H, cyclohexyl —CH$_2$).

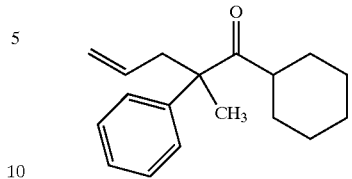

Preparation of 2-phenyl-2-methyl-4-pentenoyl cyclohexane

Scheme IV, step C; A solution of 31.39 g (0.2797 mol) of t-BuOK in 100 mL of THF was added dropwise to a solution of 55.00 g (0.2543 mol) of cyclohexyl 1-phenylethyl ketone and 26.4 mL (0.3052 mol) of allyl bromide in 136 mL of THF (cooled in a wet ice acetone bath). THF washings (16 mL) were added to the reaction mixture. The cooling bath was removed after addition. After reaction completion (2 h), the reaction mixture was quenched with 300 mL of 1 N HCl (pH=0) and extracted with 300 mL of heptane. The heptane extract was washed with 10% NaHCO$_3$ (aq) (pH=9), dried over MgSO$_4$, gravity filtered and concentrated under vacuum to afford 59.70 g (91.58%) of title compound as an amber oil: $^1$H NMR (d$^6$-DMSO): δ 7.32–7.42 (m, 2H, phenyl CH), 7.24–7.31 (m, 3H, phenyl CH), 5.34–5.47 (m, 1H, —CH=CH$_2$), 5.02 (dd, J=17.1 Hz, J=2.1 Hz, 1H, —CH=CH—H (trans)), 4.97 (ddd, J=10.2 Hz, J=2.2 Hz, J=1.0 Hz, 1H, —CH=CH—H (cis, W-coupling)), 2.66 (ddd, J=14.2 Hz, J=6.9 Hz, J=1.0 Hz, 1H, —CH$_2$CH=CH$_2$), 2.59 (ddd, J=14.2 Hz, J=7.3 Hz, J=1.0 Hz, 1H, —CH$_2$CH=CH$_2$), 2.38–2.49 (m, 1H, cyclohexyl CH), 1.48–1.69 (m, 4H, cyclohexyl —CH$_2$), 1.46 (s, 3H, —CH(CH$_3$)ph), 1.36–1.44 (m, 1H, cyclohexyl —CH$_2$), 0.82–1.36 (m, 5H, cyclohexyl —CH$_2$).

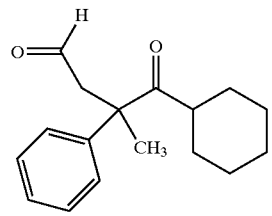

Preparation of 4-Cyclohexyl-3-methyl-4-oxo-3-phenylbutyraldehyde

Scheme IV, step D: Ozone was bubbled through a cloudy mixture of 56.50 g (0.2204 mol) of 2-phenyl-2-methyl-4-pentenoyl cyclohexane and a small amount (~10 mg) of Sudan III in 220 mL of MeOH (cooled in a dry ice acetone bath at −20° C.) for 4 h until pink color turned to pale yellow color. After all of the olefin was consumed, Me$_2$S (50 mL) was added to reaction mixture. The cooling bath was removed. The exotherm rose to 38° C. and mixture was cooled in cooling bath until there was no exotherm. Then the cooling bath was removed and the mixture was stirred overnight. The reaction solution was concentrated under vacuum with dry ice trap to collect excess Me$_2$S to afford 83.65 g of crude 4-cyclohexyl -3-methyl-4-oxo-3-phenylbutyraldehyde dimethyl acetal as a pink oil:
$^1$H NMR (d$^6$-DMSO): δ 7.34–7.39 (m, 2H, phenyl CH), 7.24–7.30 (m, 3H, phenyl CH), 3.99 (dd, J=4.2 Hz, J=5.9

Hz, 1H, CH(OCH₃)₂), 3.14 (s, 3H, CH(OCH₃)₂), 3.06 (s, 3H, CH(OCH₃)₂), 2.34–2.43 (m, 1H, cyclohexyl CH), 2.10–2.20 (m, 2H, —CH₂CH(OCH₃)₂), 1.55–1.67 (m, 1H, cyclohexyl —CH₂), 1.53 (s 3H, R₂C(CH₃)Ph), 0.80–1.52 (m, 9H, cyclohexyl —CH₂).

To a solution of 82.65 g (66.29 g, 0.2177 mol) of 4-cyclohexyl-3-methyl-4-oxo-3-phenylbutyraldehyd dimethyl acetal in 539 mL of acetone was added 539 mL of 3 N HCl (aq) at RT. After reaction completion (2 h), the mixture was concentrated to 426.5 g (or ⅓ volume) of residue (RT-40° C.). The residue contained mostly water (pH=0) and was extracted twice with 300 mL of MTBE. The MTBE extract was washed with 300 mL of 25% NaCl (aq), dried over MgSO₄, gravity filtered and concentrated to afford 54.92 g (97.65%) of title compound as a pink oil: ¹H NMR (d⁶-DMSO): δ 9.54 (t, J=2.0 Hz, 1H, —CHO), 7.36–7.45 (m, 2H, phenyl CH), 7.28–7.35 (m, 3H, phenyl CH), 2.95 (dd, J=16.6 Hz, J=1.9 Hz, 1H, CH₂CHO), 2.85 (dd, J=16.6 Hz, J=1.7 Hz, 1H, CH₂CHO), 2.41–2.49 (m, 1H, cyclohexyl CH), 1.72 (s, 3H, R₂C(CH₃)Ph), 0.85–1.66 (m, 10H, cyclohexyl —CH₂).

Preparation of final title compound 1-(2-methoxyphenyl)-4-[3-(cyclohexanecarbonyl)-3-(phenyl)butyl]piperazine Scheme IV, step E: To a slurry of 13.72 g (0.05310 mol) of 4-cyclohexyl-3-methyl-4-oxo-3-phenylbutyraldehyde and 11.57 g (0.05058 mol) of 1-(2'-methoxyphenyl)piperazine hydrochloride in 391 mL of CH₂Cl₂ was added 9.7 mL of AcOH to make the reaction mixture homogeneous. To the reaction solution was added slowly 14.63 g (0.06904 mol) of NaBH(OAc)₃. After stirring over 4 days (reaction should be complete within 2–5 h), 200 mL of 1N HCl (aq) was added to quench reaction mixture (pH=1). The mixture was extracted with 200 mL of CH₂Cl₂. The CH₂Cl₂ extract was washed again with 200 mL of 1N HCl (aq) (pH=1). Both HCl (aq) washes were combined and saved. The organic extract was washed with 200 mL of 1N NaOH (aq) (pH=14). An emulsion formed and was broken up by addition of 100 mL of water and 100 mL of MTBE. The organic phase was washed again with 200 mL of 1N NaOH (aq) (pH=14) and washed with 200 mL of 25% NaCl (aq), dried over MgSO₄, gravity filtered and concentrated to afford 22.74 g of crude title compound as an amber oil. HPLC analysis against pure standard showed that crude product oil has 13.66 g (61.71%) of title compound.

To the combined HCl wash was added 28.44 g of NaOH (s) to make mixture basic (pH=14). The cloudy mixture was extracted twice with 100 mL of CH₂Cl₂. The CH₂Cl₂ extracts were combined, washed with 25% NaCl (aq), dried over MgSO₄, gravity filtered and concentrated to afford 1.86 g of amber oil residue that contained 0.096 g (total=62.15%) of title compound and 1.05 g (10.8% recovery) of 1-(2'-methoxyphenyl)piperazine.

¹H NMR (d⁶-DMSO): δ 7.35–7.43 (m, 2H, phenyl CH), 7.26–7.32 (m, 3H, phenyl CH), 6.89–6.96 (m, 2H, phenyl CH), 6.83–6.88 (m, 2H, phenyl CH), 3.76 (s, 3H, OCH₃), 2.80–3.03 (m, 4H, piperazine CH₂), 2.34–2.49 (m, 4H, piperazine CH₂), 1.91–2.24 (m, 4H), 1.52–1.62 (m, 2H, cyclohexyl CH₂), 1.51 (s, 3H, R₂C(CH₃)Ph), 1.34–1.48 (m, 2H, cyclohexyl —CH₂), 1.13–1.27 (m, 4H, cyclohexyl —CH₂), 1.00–1.10 (m, 2H, cyclohexyl —CH₂), 0.83–1.00 (m, 1H, cyclohexyl —CH₂).

ALTERNATIVE PREPARATION OF FINAL TITLE COMPOUND

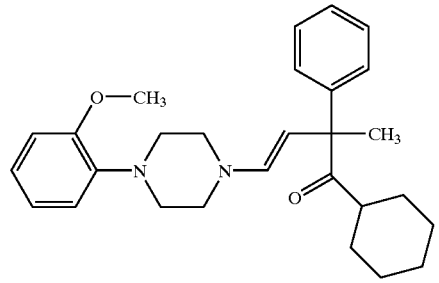

Preparation of Enamine

Scheme V, step A: To a solution of 25.00 g (0.1093 mol) of 1-(2'-methoxyphenyl)piperazine hydrochloride in 42 mL of water was added 14.5 mL (0.109 mol) of concentrated (29.4%) NH₄OH (aq) (pH=9). The mixture was extracted twice with 250 mL of 1:1 (v/v) of THF:toluene. The organic extracts were combined, dried over MgSO₄, gravity filtered and concentrated to afford 20.17 g (96.00%) of 1-(2'-methoxyphenyl)piperazine as a pale green oil: ¹H NMR (d⁶-DMSO): d 6.90–6.97 (m, 2H, phenyl CH), 6.83–6.90 (m, 3H, phenyl CH), 3.77 (s, 3H, OCH₃), 2.77–2.91 (m, 8H, piperazine CH₂), 2.49–2.53 (m, 1H, NH). A solution of 9.55 g (0.0370 mol) of 4-cyclohexyl-3-methyl-4-oxo-3-phenylbutyraldehyde in 10 mL of iPrOAc was added to 6.77 g (0.0352 mol) of neat 1-(2'-methoxyphenyl)piperazine. The mixture turned turbid, and then turned to a solid mass when 10 mL of iPrOAc was added. The solid was slurried with 45 mL of iPrOAc. After 1.5 h, reaction was complete. The solid was vacuum filtered and washed with 10 mL of iPrOAc and air dried to afford 9.81 g (64.4%) of pure enamine as an off-white powder. The filtrate was concentrated to afford 6.40 g of crude enamine;

¹H NMR (d⁶-DMSO): δ 7.31–7.43 (m, 2H, phenyl CH), 7.20–7.31 (m, 3H, phenyl CH), 6.82–7.04 (m, 4H, phenyl CH), 6.06 (d, J=14.2 Hz, 1H, CR₃CH=CHNR₂ (trans)), 4.98 (d, J=14.2 Hz, 1H, CR₃CH=CH NR₂(trans)), 3.80 (s, 3H, OCH₃), 2.93–3.15 (m, 8H, piperazine CH₂), 2.38–2.49 (m, 1H, cyclohexyl CH), 1.59–1.72 (m, 2H, cyclohexyl CH₂), 1.47–1.59 (m, 2H, cyclohexyl —CH₂), 1.40 (s, 3H, R₂C(CH₃)Ph), 1.21–1.34 (m, 3H, cyclohexyl —CH₂), 1.03–1.21 (m, 2H, cyclohexyl —CH₂), 0.83–1.03 (m, 1H, cyclohexyl —CH₂).

Preparation of Final Title Compound

Scheme V, step B: To 5.35 g (0.00101 mol) of 5% Pd/C in a 500 mL Parr bottle chilled in an ice bath was added 8.68 g (0.0201 mol) of above-formed enamine. To the solid mixture was added 40 mL of IPA cooled in a freezer (−22° C.). H₂ was introduced at 50 psi and mixture was shaken for 2 day at RT to complete reaction. The black slurry was vacuum filtered and concentrated to afford 8.70 g of a colorless oil. The Pd/C catalyst was washed with 50 mL of IPA with stirring. The black slurry was vacuum filtered. The filtrate was combined with 8.70 g of residue and concentrated to afford 10.03 g of the final title compound as a colorless oil.

Additional compounds included with the scope of the present invention, which can be prepared by one of ordinary skill in the art in a manner analogous to the procedures described above, are as follows:

10) (+)-1-(2-methoxyphenyl)-4-[3-(cyclohexanecarbonyl)-3-(phenyl)butyl]piperazine dihydrobromide;
11) (+)-1-(2-methoxyphenyl)-4-[3-(cyclohexanecarbonyl)-3-(phenyl)butyl]piperazine monohydrobromide;
12) (+)-1-(2-methoxyphenyl)-4-[3-(cyclohexanecarbonyl)-3-(phenyl)butyl]piperazine succinate, 1:1;
13) (+)-1-(2-methoxyphenyl)-4-[3-(cyclohexanecarbonyl)-3-(phenyl)butyl]piperazine succinate, 2:1;
14) (+)-1-(2-methoxyphenyl)-4-[3-(cyclohexanecarbonyl)-3-(phenyl)butyl]piperazine phosphate;
15) (+)-1-(2-methoxyphenyl)-4-[3-(cyclohexanecarbonyl)-3-(phenyl)butyl]piperazine d-tartrate;
16) (+)-1-(2-methoxyphenyl)-4-[3-(cyclohexanecarbonyl)-3-(phenyl)butyl]piperazine l-tartrate;
17) (+)-1-(2-methoxyphenyl)-4-[3-(cyclohexanecarbonyl)-3-(phenyl)butyl]piperazine maleate;

Serotonin 1A Receptor Activity

The compounds of the present invention are selective antagonists at the serotonin 1A receptor. Previously known compounds with 1A receptor activity typically have the disadvantage of possessing other central nervous system activities as well. It is now well understood by pharmacologists and physicians that pharmaceuticals which have a single physiological activity, or which are much more active in the desired activity than in their other activities, are much more desirable for therapy than are compounds (pindolol for example) which have multiple activities at about the same dose.

Many other known serotonin receptor 1A antagonists typically have α-adrenergic, β-adrenergic or dopamine-2 activity as well, and are therefore nonselective for 1A activity.

The $5\text{-HT}_{1A}$ receptor binding potency of the present compounds has been measured by a modification of the binding assay described by Taylor, et al. (*J. Pharmacol. Exp. Ther.*, 236, 118–125, 1986); and Wong, et al., *Pharm. Biochem. Behav.*, 46, 173–77 (1993). Membranes for the binding assay were prepared from male Sprague-Dawley rats. (150–250 g). The animals were killed by decapitation, and the brains were rapidly chilled and dissected to obtain the hippocampi. Membranes from the hippocampi were either prepared that day, or the hippocampi were stored frozen (−70°) until the day of preparation. The membranes were prepared by homogenizing the tissue in 40 volumes of ice-cold Tris-Hydrochloric acid buffer (50 mM, pH 7.4 at 22°) using a homogenizer for 15 seconds, and the homogenate was centrifuged at 39800×g for 10 minutes. The resulting pellet was then resuspended in the same buffer, and the centrifugation and resuspension process was repeated three additional times to wash the membranes. Between the second and third washes the resuspended membranes were incubated for 10 minutes at 37° to facilitate the removal of endogenous ligands. The final pellet was resuspended in 67 mM Tris-Hydrochloric acid, pH 7.4, to a concentration of 2 mg of tissue original wet weight/200 µl. This homogenate was stored frozen (−70°) until the day of the binding assay. Each tube for the binding assay had a final volume of 800 µl and contained the following: Tris-Hydrochloric acid (50 mM), pargyline (10 µM), $CaCl_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes were incubated for either 10 minutes or 15 minutes at 37°, and the contents were then rapidly filtered through GF/B filters (pretreated with 0.5% polyethylenimine), followed by four one-ml washes with ice-cold buffer. The radioactivity trapped by the filters was quantitated by liquid scintillation spectrometry, and specific [$^3$H]8-OH-DPAT binding to the $5\text{-HT}_{1A}$ sites was defined as the difference between [$^3$H]8-OH-DPAT bound in the presence and absence of 10 µM 5-HT.

$IC_{50}$ values, i.e., the concentration required to inhibit 50% of the binding, were determined from 12-point competition curves using nonlinear regression (SYSTAT, SYSTAT, Inc., Evanston, Ill.). $IC_{50}$ values were converted to $K_i$ values using the Cheng-Prusoff equation (*Biochem. Pharmacol.*, 22, 3099–3108 (1973). All experiments were performed in triplicate.

Additional binding assays of some of the present compounds have been carried out by an assay method which uses a cloned cell line which expresses the serotonin 1A receptor, rather than the hippocampal membranes. Such cloned cell lines have been described by Fargin, et al., *J.Bio. Chem.*, 264, 14848–14852 (1989), Aune, et al., *J. Immunology*, 151, 1175–1183 (1993), and Raymond, et al., *Naunyn-Schmiedeberg's Arch. Pharmacol.*, 346, 127–137 (1992). Results from the cell line assay are substantially in agreement with results from the hippocampal membrane assay.

$5HT_{1a}$ Antagonist, in vivo Tests a) $5HT_{1a}$ Antagonism Subcutaneous Test

Compounds were tested over a range of subcutaneous doses for activity in blocking the 8-OH-DPAT induced behaviors and hypothermia. Lower lip retraction (LLR) and flat body posture (FBP) were recorded in male Sprague Dawley rats (~250 grams from Harlan Sprague Dawley). Both LLR and FBP were measured on a scale of 0–3 (Wolff et al, 1997). In the LLR behavioral assay, "0" indicated normal lip position; "1" indicated a slight separation of the lips; "2" indicated that the lips were open with some teeth visible; "3" indicated that the lips were fully open with all the front teeth exposed. In the FBP assay, a score of "0" indicated normal body posture; "1" indicated that the stomach was on the floor with the back in its normal rounded position; "2" indicated that the stomach was on the floor with the back straightened and rising from the shoulders to the hips; "3" indicated that the stomach was pressed into the floor and the back was flattened with the shoulders and hips even. Core body temperature was recorded by rectal probe inserted 5.0 cm immediately after the behavioral measures. Rats were injected subcutaneous with compound (at 0, 0.3, 1.0 and 3.0 mg/kg) 35 minutes before scoring and the 8-OH-DPAT (0.1 mg/kg subcutaneous) was injected 20 minutes before scoring.

b) $5HT_{1a}$ Agonist Subcutaneous Test

The compounds were also tested at a high dose of 10 mg/kg subcutaneous alone to see if they induced $5HT_{1a}$ agonist-like hypothermia.

The potent serotonin 1A receptor activity of the present compounds gives them a number of pharmaceutical and therapeutic applications. One of those applications is a method of assisting people who are dependent on the use of tobacco or nicotine to break the habit.

Tobacco or Nicotine Withdrawal

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user is fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such patients can be assisted to reduce and even eliminate entirely their dependence on nicotine in all forms.

It will be understood that the present invention is useful for preventing or alleviating the withdrawal symptoms which afflict patients who are trying to eliminate or reduce their use of tobacco or nicotine. The common withdrawal symptoms of such people include, at least, irritability, anxiety, restlessness, lack of concentration, insomnia, nervous tremor, increased hunger and weight gain, lightheadedness, and the craving for tobacco or nicotine. The prevention or alleviation of such symptoms, when they are caused by or occur in conjunction with ceasing or reducing the patient's use of tobacco or nicotine is a desired result of the present invention and an important aspect of it.

The present invention is carried out by administering an effective amount of a compound of Formula I or formula Ia to a patient who is in need of or carrying out a reduction or cessation of tobacco or nicotine use.

As used herein, the term "patient" refers to a warm-blooded animal, such as a mammal. Included within the term "patient" are humans, dogs, rats, mice and the like. It is understood that the preferred patient is a human.

An effective amount of a compound of Formula I or formula Ia, is the amount, or dose, of the compound which provides the desired effect in the patient under diagnosis or treatment. The dose of compound of Formula I or formula Ia to be administered, is effective over a wide dosage range, in general, it is from about 1 to about 200 mg/day; as usual, the daily dose may be administered in a single bolus, or in divided doses, depending on the judgment of the physician in charge of the case. A more preferred range of doses is from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day. It will be understood that the dose for a given patient is always to be set by the judgment of the attending physician, and that the dose is subject to modification based on the size of the patient, the lean or fat nature of the patient, the characteristics of the particular compound chosen, the intensity of the patient's tobacco habit, the intensity of the patient's withdrawal symptoms, and psychological factors which may affect the patient's physiological responses.

The effect of the compounds in alleviating the symptoms of nicotine withdrawal was evaluated in rats by an auditory startle test, which was carried out as follows.

Procedures for Nicotine Withdrawal Studies

Animals: Male Long Evans rats were individually housed in a controlled environment on a 12 hour light-dark cycle and were given free access to food (Purina Rodent Chow) and water. All treatment groups contained 8–10 rats.

Chronic Nicotine Treatment: Rats were anesthetized with halothane and Alzet™ osmotic minipumps (Alza Corporation, Palo Alto, Calif., Model 2ML2) were implanted subcutaneously. Nicotine ditartrate was dissolved in physiological saline. Pumps were filled with either nicotine ditartrate (6 mg/kg base/day) or physiological saline. Twelve days following implantation of pumps, rats were anesthetized with halothane and the pumps were removed.

Auditory Startle Response: The sensory motor reactions [auditory startle response (peak amplitude Vmax)] of individual rats was recorded using San Diego Instruments startle chambers (San Diego, Calif.). Startle sessions consisted of a 5-minute adaptation period at a background noise level of $70\pm3$ dBA immediately followed by 25 presentations of auditory stimuli ($120\pm2$ dBA noise, 50 ms duration) presented at 8-second intervals. Peak startle amplitudes were then averaged for all 25 presentations of stimuli for each session. Auditory startle responding was evaluated daily at 24 hour intervals on days 1–4 following nicotine withdrawal.

Combination with Reuptake Inhibitors

A further application of the compounds of Formula I or formula Ia is their use in combination with a serotonin reuptake inhibitor to further potentiate the action of those drugs by increasing the availability of serotonin, as well as norepinephrine and dopamine, in the brain of patients to whom the drug combination is administered. Typical and appropriate serotonin reuptake inhibitors (SRI) are fluoxetine, duloxetine, venlafaxine, milnacipran, citalopram, fluvoxamine and paroxetine. Accordingly, the present invention provides a method for potentiating the action of a serotonin reuptake inhibitor, particularly one of the group consisting of fluoxetine, duloxetine, venlafaxine, milnacipran, citalopram, fluvoxamine and paroxetine, in increasing the availability of serotonin, norepinephrine and dopamine in the brain, comprising administering said serotonin reuptake inhibitor in combination with a compound of Formula I or formula Ia. The invention also provides pharmaceutical compositions which comprise a serotonin reuptake inhibitor in combination with a compound of Formula I or formula Ia, and a method of treating a pathological condition which is created by or is dependent upon decreased availability of serotonin, dopamine or norepinephrine, which method comprises administering the same adjunctive therapy to a patient in need of such treatment.

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.*, 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and is the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., Neuropharmacology 24, 1211–19 (1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen, et al., Eur. J. Pharmacol., 41, 153 (1977), and reports of its clinical effectiveness in depression may be found in Dufour, et al., Int. Clin. Psychopharmacol., 2, 225 (1987), and Timmerman, et al., ibid., 239.

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen, et al., Brit. J. Pharmacol., 60, 505 (1977); and De Wilde, et al., J. Affective Disord., 4, 249 (1982); and Benfield, et al., Drugs, 32, 313 (1986).

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, Eur. J. Pharmacol., 47, 351 (1978); Hassan, et al., Brit. J. Clin. Pharmacol., 19, 705 (1985); Laursen, et al., Acta Psychiat. Scand., 71, 249 (1985); and Battegay, et al., Neuropsychobiology, 13, 31 (1985).

All of the U.S. patents which have been mentioned above in connection with compounds used in the present invention are incorporated herein by reference.

In general, combinations and methods of treatment using fluoxetine or duloxetine as the SRI are preferred.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred dosages, are provided. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 5 to about 100 mg once/day; preferred, from about 50 to about 300 mg once/day.

In more general terms, one would create a combination of the present invention by choosing a dosage of SRI according to the spirit of the above guideline, and choosing a dosage of the compound of Formula I or formula Ia in the ranges taught above.

The adjunctive therapy of the present invention is carried out by administering a SRI together with a compound of Formula I or formula Ia in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for the adjunctive combination to be administered as a single pharmaceutical composition, and so pharmaceutical compositions incorporating both a SRI and a compound of Formula I or formula Ia are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

As stated above, the benefit of the adjunctive therapy is its ability to augment the increase in availability of serotonin, norepinephrine and dopamine caused by the SRI compounds, resulting in improved activity in treating the various conditions described below in detail. The increase in availability of serotonin is particularly important and is a preferred aspect of the invention. Further, the invention provides a more rapid onset of action than is usually provided by treatment with the SRI alone.

Preferred pathological conditions to be treated by the present method of adjunctive therapy include depression, bulimia, obsessive-compulsive disease and obesity. Another preferred condition more specific to combinations including preferably duloxetine but also venlafaxine and milnacipran is urinary incontinence.

Depression in its many variations has recently become much more visible to the general public than it has previously been. It is now recognized as an extremely damaging disorder, and one that afflicts a surprisingly large fraction of the population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago. Duloxetine is in clinical trials for the treatment of depression.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the present adjunctive therapy method and compositions.

Obsessive-compulsive disease appears in a great variety of degrees and symptoms, generally linked by the patient's uncontrollable urge to perform needless, ritualistic acts. Acts of acquiring, ordering, cleansing and the like, beyond any rational need or rationale, are the outward characteristic of the disease. A badly afflicted patient may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese patient to lose weight, with the resulting benefit to the patient's circulation and heart condition, as well as general well being and energy.

Urinary incontinence is classified generally as stress or urge incontinence, depending on whether its root cause is the inability of the sphincter muscles to keep control, or the overactivity of the bladder muscles. Duloxetine controls both types of incontinence, or both types at once, and so is important to the many people who suffer from this embarrassing and disabling disorder.

The present combination is useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00
migraine
pain, particularly neuropathic pain
bulimia, ICD 307.51, DSM 307.51
premenstrual syndrome or late luteal phase syndrome, DSM 307.90
alcoholism, ICD 305.0, DSM 305.00 & 303.90
tobacco abuse, ICD 305.1, DSM 305.10 & 292.00
panic disorder, ICD 300.01, DSM 300.01 & 300.21
anxiety, ICD 300.02, DSM 300.00
post-traumatic syndrome, DSM 309.89
memory loss, DSM 294.00
dementia of aging, ICD 290
social phobia, ICD 300.23, DSM 300.23
attention deficit hyperactivity disorder, ICD 314.0
disruptive behavior disorders, ICD 312
impulse control disorders, ICD 312, DSM 312.39 & 312.34
borderline personality disorder, ICD 301.83, DSM 301.83
chronic fatigue syndrome
premature ejaculation, DSM 302.75
erectile difficulty, DSM 302.72
anorexia nervosa, ICD 307.1, DSM 307.10
disorders of sleep, ICD 307.4
autism
mutism
trichotillomania Further, the compounds of Formula I or formula Ia are particularly useful for alleviating the symptoms of smoking cessation or nicotine withdrawal when administered in combination with a serotonin reuptake inhibitor. The SRI's to be used in this treatment method, and the administration methods and formulations, are as described above. The use of the present compounds with SRI's in patients striving to stop use of tobacco or nicotine provides surprisingly complete alleviation of the usual painful and damaging symptoms of such patients, including nervousness, irritability, craving, excessive appetite, anxiety, depression in many forms, inability to concentrate, and the like.

Therapeutic Applications

The compounds of Formula I or formula Ia are useful for other important therapeutic purposes, as well as in combination with SRIs and in nicotine withdrawal or smoking cessation cases. In particular, the compounds are useful for antagonism at the serotonin 1A receptor and accordingly are used for the treatment or prevention of conditions caused by or affected by excessive activity of that receptor.

More particularly, the compounds of Formula I or formula Ia are useful in the treatment of anxiety, depression, hypertension, cognitive disorders, psychosis, sleep disorders, gastric motility disorders, sexual dysfunction, brain trauma, memory loss, appetite disorders and obesity, substance abuse, obsessive-compulsive disease, panic disorder and migraine.

Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02. A further particularly noted disorder is depression and the group of depression-related disorders, which are discussed above in the discussion of adjunctive therapy with SRIs.

Pharmaceutical Compositions

It is customary to formulate pharmaceuticals for administration, to provide control of the dosage and stability of the product in shipment and storage, and the usual methods of formulation are entirely applicable to the compounds of Formula I and formula Ia. Such compositions, comprising at least one pharmaceutically acceptable carrier, are valuable and novel because of the presence of the compounds of Formula I or formula Ia therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used, including tablets, chewable tablets, capsules, solutions, parenteral solutions, intranasal sprays or powders, troches, suppositories, transdermal patches and suspensions. In general, compositions contain from about 0.5% to about 50% of the compound in total, depending on the desired dose and the type of composition to be used. The amount of the compound of Formula I or formula Ia, however, is best defined as the effective amount, that is, the amount of the compound which provides the desired dose to the patient in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with innumerable pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Example 1 | 20 mg |
| Starch, dried | 200 mg |
| Magnesium stearate | 10 mg |
| Total | 230 mg |

Formulation 2

A tablet is prepared using the ingredients below:

|  | Quantity (mg/capsule) |
| --- | --- |
| Example 2 | 10 mg |
| Cellulose, microcrystalline | 400 mg |
| Silicon dioxide, fumed | 10 mg |
| Stearic acid | 5 mg |
| Total | 425 mg |

The components are blended and compressed to form tablets each weighing 425 mg.

Formulation 3

Tablets, each containing 10 mg of active ingredient, are made as follows:

| Example 3 | 10 mg |
| --- | --- |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Formulation 4

Capsules, each containing 30 mg of active ingredient, are made as follows:

| | |
|---|---|
| Example 4 | 30 mg |
| Starch | 59 mg |
| Microcrystalline cellulose | 59 mg |
| Magnesium stearate | 2 mg |
| Total | 150 mg |

The active ingredient, cellulose, starch, and magnesium stearate are blended, passed through a No. 45 mesh U.S. sieve, and filled into hard gelatin capsules in 150 mg quantities.

Formulation 5

Suppositories, each containing 5 mg of active ingredient, are made as follows:

| | |
|---|---|
| Example 5 | 5 mg |
| Saturated fatty acid glycerides | 2,000 mg |
| Total | 2,005 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

Formulation 6

Suspensions, each containing 10 mg of active ingredient per 5 ml dose, are made as follows:

| | |
|---|---|
| Example 6 | 10 mg |
| Sodium carboxymethyl cellulose | 50 mg |
| Syrup | 1.25 ml |
| Benzoic acid solution | 0.10 ml |
| Flavor | q.v. |
| Color | q.v. |
| Purified water to total | 5 ml |

The active ingredient is passed through a No. 45 mesh U.S. sieve and mixed with the sodium carboxymethyl cellulose and syrup to form a smooth paste. The benzoic acid solution, flavor and color are diluted with a portion of the water and added, with stirring. Sufficient water is then added to produce the required volume.

Formulation 7

An intravenous formulation may be prepared as follows:

| | |
|---|---|
| Example 7 | 10 mg |
| Isotonic saline | 1,000 ml |

Formulation 8

Hard gelatin capsules are prepared in a manner analogous to formulation 1 using the following ingredients:

| | Quantity (mg/capsule) |
|---|---|
| (+)-1-(2-Methoxyphenyl)-4-[3-(cyclohexanecarbonyl)-3-(phenyl)butyl]piperazine HCl | 20 mg |
| Starch, dried | 200 mg |
| Magnesium stearate | 10 mg |
| Total | 230 mg |

Formulation 9

A tablet is prepared using the ingredients below:

| | Quantity (mg/capsule) |
|---|---|
| (+)-1-(2-Methoxyphenyl)-4-[3-(cyclohexanecarbonyl)-3-(phenyl)butyl] piperazine HCl | 10 mg |
| Cellulose, microcrystalline | 400 mg |
| Silicon dioxide, fumed | 10 mg |
| Stearic acid | 5 mg |
| Total | 425 mg |

The components are blended and compressed to form tablets each weighing 425 mg in a manner analogous to formulation 2.

Formulation 10

Tablets, each containing 10 mg of active ingredient, are made as follows:

| | |
|---|---|
| (+)-1-(2-Methoxyphenyl)-4-[3-(cyclohexanecarbonyl)-3-(phenyl)butyl]piperazine HCl | 10 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 100 mg |

The active ingredient, starch and cellulose are passed through a No. 45 mesh U.S. sieve and mixed thoroughly. The aqueous solution containing polyvinyl-pyrrolidone is mixed with the resultant powder, and the mixture then is passed through a No. 14 mesh U.S. sieve. The granules so produced are dried at 50° C. and passed through a No. 18 mesh U.S. Sieve. The sodium carboxymethyl starch, magnesium stearate and talc, previously passed through a No. 60 mesh U.S. sieve, are then added to the granules which, after mixing, are compressed on a tablet machine to yield tablets each weighing 100 mg.

Formulation 11

Capsules, each containing 30 mg of active ingredient, are made as follows in a manner analogous to formulation 4:

| | |
|---|---|
| (+)-1-(2-Methoxyphenyl)-4-[3-cyclohexanecarbonyl)-3-(phenyl)butyl]piperazine HCl | 30 mg |
| Starch | 59 mg |
| Microcrystalline cellulose | 59 mg |
| Magnesium stearate | 2 mg |
| Total | 150 mg |

What is claimed is:

1. A process for the preparation of a compound of the formula

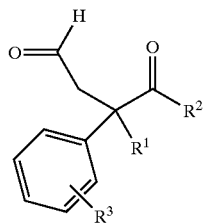

formula II wherein
- $R^1$ is hydrogen, $(C_1-C_6)$alkyl, $(C_1-C_6)$alkoxy, or $(C_1-C_6)$alkylthio;
- $R^2$ is phenyl, naphthyl or $(C_3-C_{12})$cycloalkyl substituted with one or two substituents selected from the group consisting of hydrogen, $(C_1-C_6)$alkyl, $(C_1-C_6)$alkoxy, $(C_1-C_6)$alkylthio, $(C_2-C_6)$alkenyl, $(C_2-C_6)$alkynyl, $(C_1-C_6)$alkylhalo, $(C_3-C_8)$cycloalkyl, $(C_3-C_8)$cycloalkenyl or halo;
- $R^3$ is selected from the group consisting of hydrogen, $(C_1-C_6)$alkyl, $(C_1-C_6)$alkoxy, $(C_1-C_6)$alkylthio, $(C_2-C_6)$alkenyl, $(C_2-C_6)$alkynyl, $(C_1-C_6)$alkylhalo, $(C_3-C_8)$cycloalkyl, $(C_3-C_8)$cycloalkenyl or halo, comprising, treating a compound of formula III

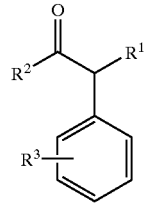

formula III wherein $R^1$, $R^2$ and $R^3$ are described as above, with a base and a compound of formula IV:

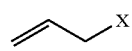

formula IV wherein X is a leaving group, to provide the compound of formula V

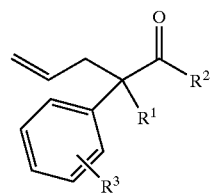

formula V and oxidizing the compound of formula V with an oxidizing agent to provide the compound of formula II.

2. A process according to claim 1 wherein
$R^1$ is $CH_3$;
$R^2$ is cyclohexyl; and
$R^3$ is hydrogen.

3. A process according to claim 2 wherein
X is Br or Cl.

4. A process according to claim 3 wherein the oxidizing agent is ozone.

5. A process according to claim 4 wherein the base is potassium tert-butoxide.

* * * * *